United States Patent
Scott et al.

(10) Patent No.: US 10,639,038 B2
(45) Date of Patent: May 5, 2020

(54) STAPLE CARTRIDGE WITH SHORT CIRCUIT PREVENTION FEATURES

(71) Applicant: ETHICON LLC, Guaynabo, PR (US)

(72) Inventors: Gregory G. Scott, Cincinnati, OH (US); Stephen D. Geresy, West Chester, OH (US); Yvan D. Nguetio Tchoumkeu, Blue Ash, OH (US); Laura A. Schoettmer, Cincinnati, OH (US); Andrew Kolpitcke, Centerville, OH (US); Sarah A. Worthington, Maineville, OH (US); Joshua P. Morgan, Benton, KY (US); Scott A. Jenkins, Mason, OH (US); Nicholas D. Courtwright, Villa Hills, KY (US); Alexander R. Cuti, Cincinnati, OH (US); Taylor W. Aronhalt, Loveland, OH (US); Jeffery D. Bruns, Cincinnati, OH (US); John E. Brady, Liberty Township, OH (US); Nichole Y. Kwee, Cincinnati, OH (US); Gregory J. Bakos, Mason, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 132 days.

(21) Appl. No.: 15/934,173

(22) Filed: Mar. 23, 2018

(65) Prior Publication Data
US 2019/0290271 A1 Sep. 26, 2019

(51) Int. Cl.
*A61B 17/072* (2006.01)
*A61B 18/14* (2006.01)
(Continued)

(52) U.S. Cl.
CPC .. *A61B 17/07207* (2013.01); *A61B 17/07292* (2013.01); *A61B 17/068* (2013.01);
(Continued)

(58) Field of Classification Search
CPC ............ A61B 17/072; A61B 17/07207; A61B 17/07292; A61B 17/115; A61B 17/068;
(Continued)

(56) References Cited

U.S. PATENT DOCUMENTS 5,529,235 A * 6/1996 Boiarski ................ A61B 90/98
227/175.1
5,624,452 A * 4/1997 Yates .................... A61B 17/072
606/139
(Continued)

FOREIGN PATENT DOCUMENTS

EP 2 165 664 A2 3/2010
EP 2 837 355 A2 2/2015
(Continued)

OTHER PUBLICATIONS

Hollister, S., "Waterproofing explained: How Apple, Samsung and Sony keep the liquid out," clnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.
(Continued)

*Primary Examiner* — Scott A Smith
(74) *Attorney, Agent, or Firm* — Frost Brown Todd LLC

(57) ABSTRACT

A surgical instrument includes a body, a shaft assembly, an end effector, and an electrical contact assembly. The body includes a power source. The shaft assembly extends distally from the body, the end effector is distal of the shaft assembly. The end effector includes a channel assembly and a cartridge assembly. The cartridge assembly may selectively couple
(Continued)

with the channel assembly. The cartridge assembly includes an electrically activated component. The electrical contact assembly is configured to electrically couple the power source with the electrically activated component. The electrical contact assembly includes a first electrical contact associated with the channel assembly, a second electrical contact associated with the channel assembly, and a hydrophobic layer extending between the first electrical contact and the second electrical contact.

20 Claims, 25 Drawing Sheets

(51) Int. Cl.
    *A61B 17/00*          (2006.01)
    *A61B 90/92*          (2016.01)
    *A61B 90/00*          (2016.01)
    *A61B 90/98*          (2016.01)
    *A61B 17/068*        (2006.01)

(52) U.S. Cl.
    CPC ......... *A61B 17/072* (2013.01); *A61B 18/1445* (2013.01); *A61B 90/92* (2016.02); *A61B 90/98* (2016.02); *A61B 2017/00017* (2013.01); *A61B 2017/00022* (2013.01); *A61B 2017/00026* (2013.01); *A61B 2017/00039* (2013.01); *A61B 2017/0046* (2013.01); *A61B 2017/00057* (2013.01); *A61B 2017/00398* (2013.01); *A61B 2017/00464* (2013.01); *A61B 2017/00477* (2013.01); *A61B 2017/00734* (2013.01); *A61B 2017/00862* (2013.01); *A61B 2017/00876* (2013.01); *A61B 2017/00929* (2013.01); *A61B 2017/00938* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2090/0803* (2016.02)

(58) Field of Classification Search
    CPC ........... A61B 2017/00017; A61B 2017/00022; A61B 2017/07214; A61B 2017/00398; A61B 2017/0046; A61B 2017/00477
    USPC .............. 227/19, 175.1, 175.2, 176.1, 180.1; 606/1, 49, 139, 219
    See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,817,093 A | 10/1998 | Williamson, IV et al. | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,602,252 B2* | 8/2003 | Mollenauer | A61B 17/07207 227/175.1 |
| 6,783,524 B2 | 8/2004 | Anderson et al. | |
| 7,147,138 B2* | 12/2006 | Shelton, IV | A61B 17/07207 227/176.1 |
| 7,404,508 B2 | 7/2008 | Smith et al. | |
| 7,506,790 B2* | 3/2009 | Shelton, IV | A61B 17/07207 227/175.1 |
| 7,524,320 B2 | 4/2009 | Tierney et al. | |
| 7,559,452 B2* | 7/2009 | Wales | A61B 17/068 227/175.1 |
| 7,691,098 B2 | 4/2010 | Wallace et al. | |
| 7,721,930 B2 | 5/2010 | McKenna et al. | |
| 7,784,663 B2* | 8/2010 | Shelton, IV | A61B 17/072 227/175.1 |
| 7,806,891 B2 | 10/2010 | Nowlin et al. | |
| 8,408,439 B2 | 4/2013 | Huang et al. | |
| 8,414,577 B2* | 4/2013 | Boudreaux | A61B 17/07207 606/34 |
| 8,453,914 B2 | 6/2013 | Laurent et al. | |
| 8,475,474 B2* | 7/2013 | Bombard | A61B 17/115 227/178.1 |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,608,045 B2 | 12/2013 | Smith et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,905,977 B2* | 12/2014 | Shelton | A61B 17/07207 604/131 |
| 8,955,732 B2* | 2/2015 | Zemlok | A61B 17/072 227/176.1 |
| 8,991,678 B2 | 3/2015 | Wellman et al. | |
| 9,072,535 B2 | 7/2015 | Shelton, IV et al. | |
| 9,186,142 B2 | 11/2015 | Fanelli et al. | |
| 9,301,759 B2 | 4/2016 | Spivey et al. | |
| 9,332,974 B2* | 5/2016 | Henderson | A61B 17/00491 |
| 9,345,481 B2 | 5/2016 | Hall et al. | |
| 9,724,094 B2 | 8/2017 | Baber et al. | |
| 9,795,379 B2 | 10/2017 | Leimbach et al. | |
| 9,839,425 B2 | 12/2017 | Zergiebel et al. | |
| 9,913,642 B2 | 3/2018 | Leimbach et al. | |
| 2014/0263541 A1 | 9/2014 | Leimbach et al. | |
| 2014/0263552 A1 | 9/2014 | Hall et al. | |
| 2016/0066911 A1 | 3/2016 | Baber et al. | |
| 2016/0310134 A1 | 10/2016 | Contini et al. | |
| 2017/0209145 A1 | 7/2017 | Swayze et al. | |

FOREIGN PATENT DOCUMENTS

| | | |
|---|---|---|
| EP | 2 839 797 A2 | 2/2015 |
| EP | 2 923 661 A2 | 9/2015 |
| EP | 3 338 693 A2 | 6/2018 |
| EP | 3 420 918 A1 | 1/2019 |
| WO | WO 2015/153642 A1 | 10/2015 |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,139, filed Mar. 23, 2018.
U.S. Appl. No. 15/934,148, filed Mar. 23, 2018.
U.S. Appl. No. 15/934,160, filed Mar. 23, 2018.
U.S. Appl. No. 15/934,166, filed Mar. 23, 2018.
U.S. Appl. No. 15/934,180, filed Mar. 23, 2018.
U.S. Appl. No. 15/934,190, filed Mar. 23, 2018.
European Search Report, Extended, and Written Opinion dated Jun. 28, 2019 for Application No. EP 19164720.5, 10 pgs.
International Search Report and Written Opinion dated Jul. 2, 2019 for Application No. PCT/IB2019/052282, 13 pgs.

* cited by examiner

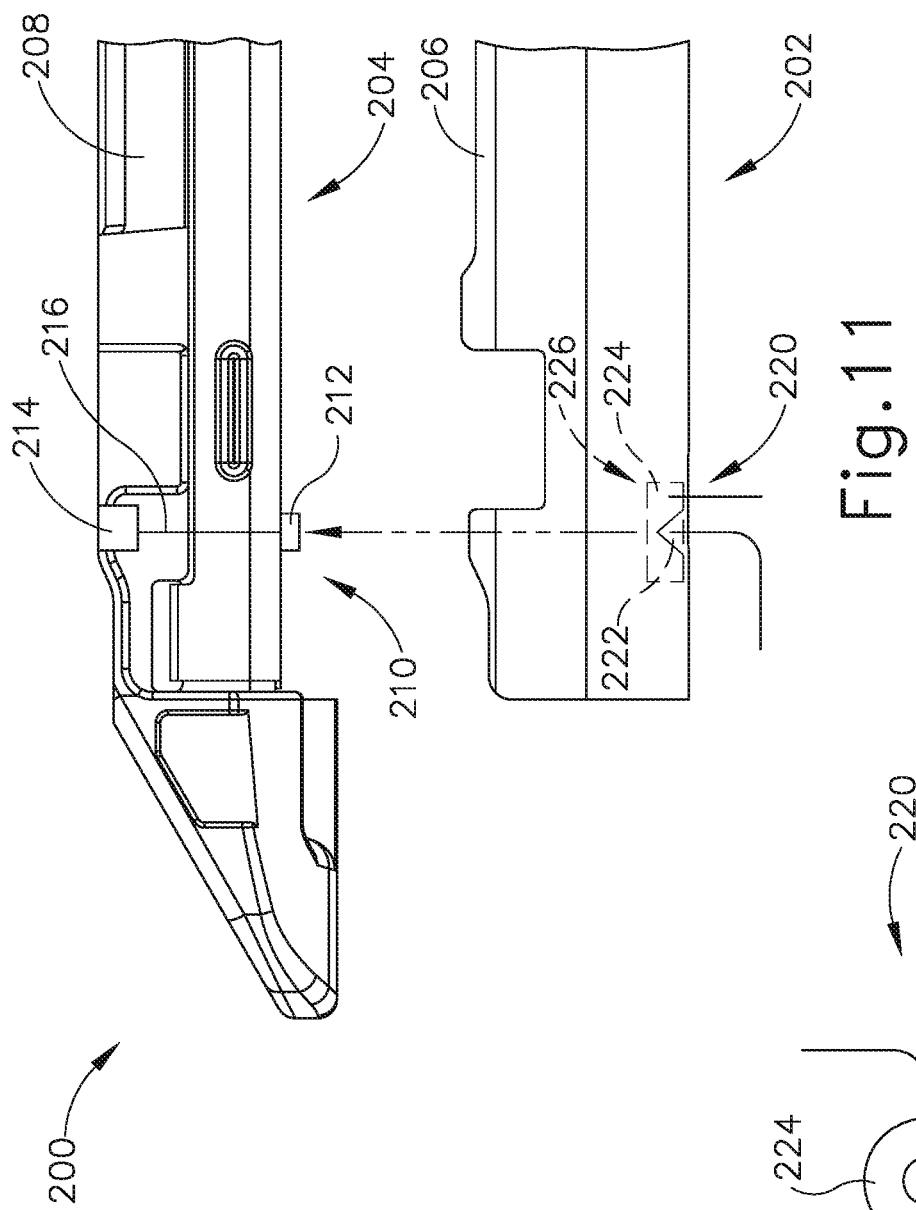
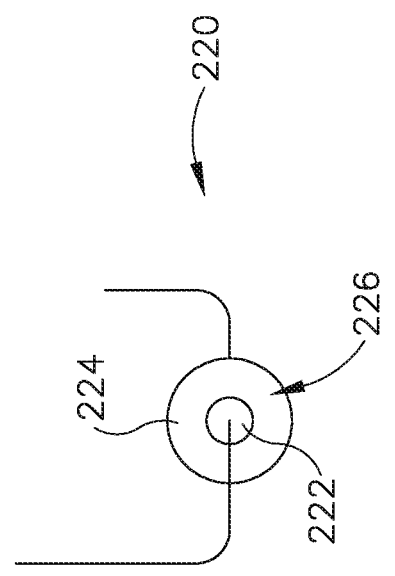
Fig.10
Fig.11

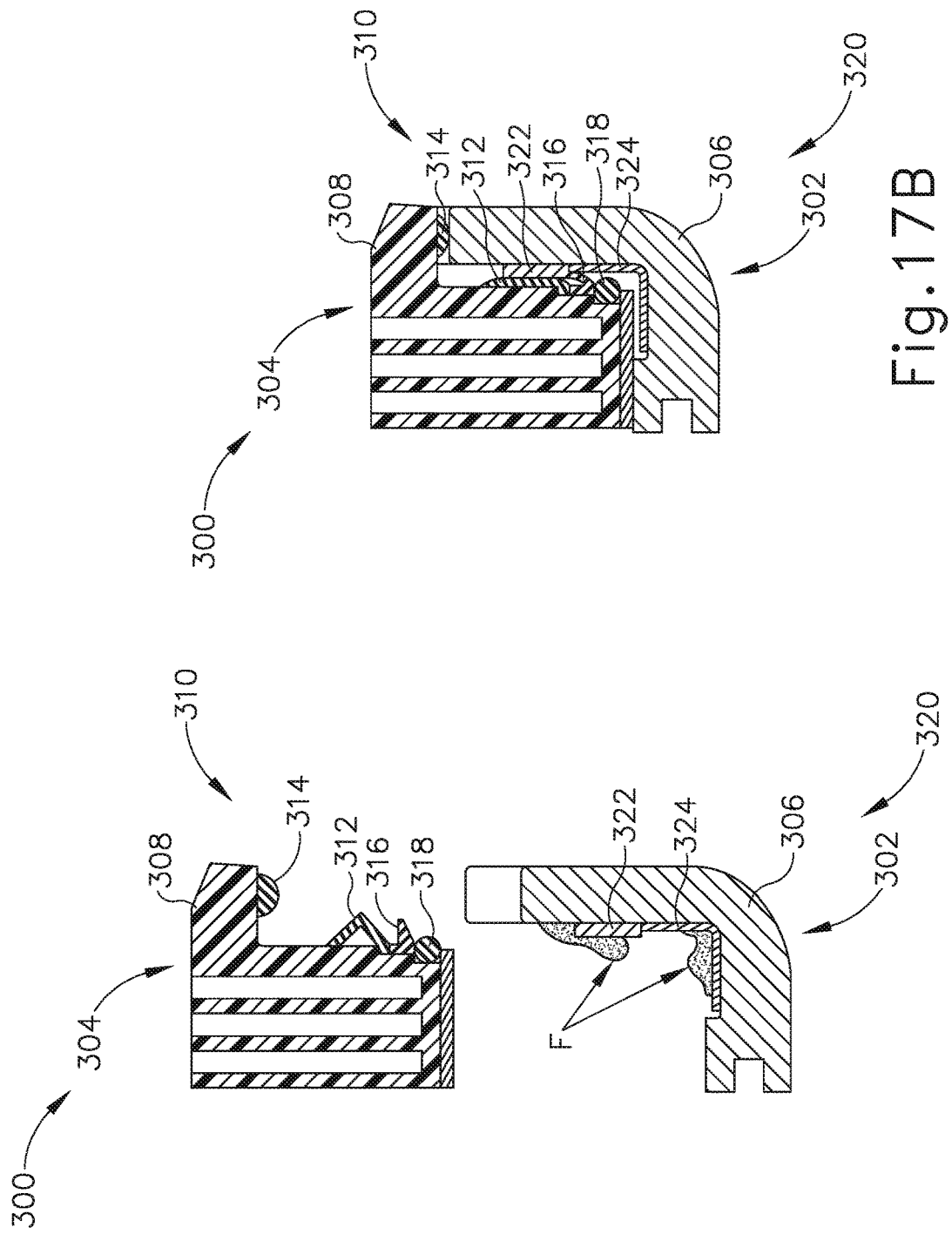

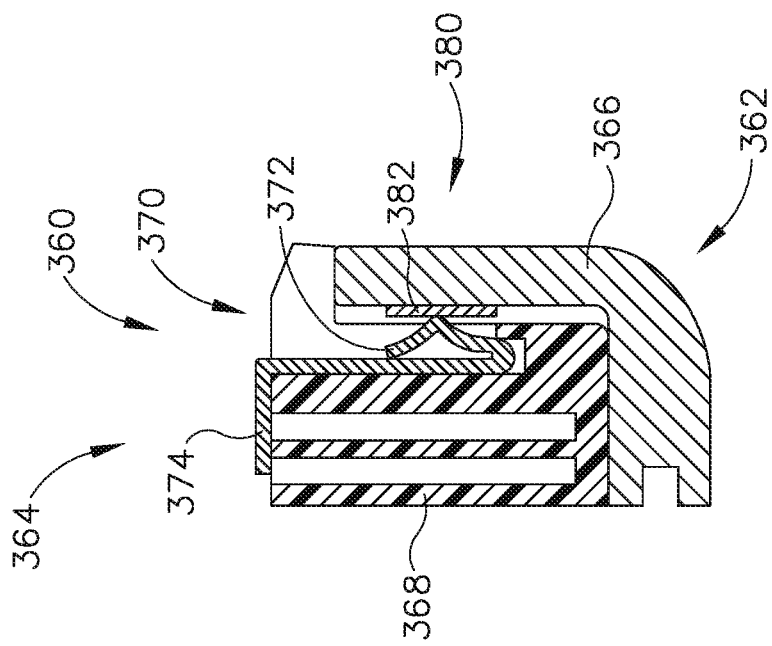
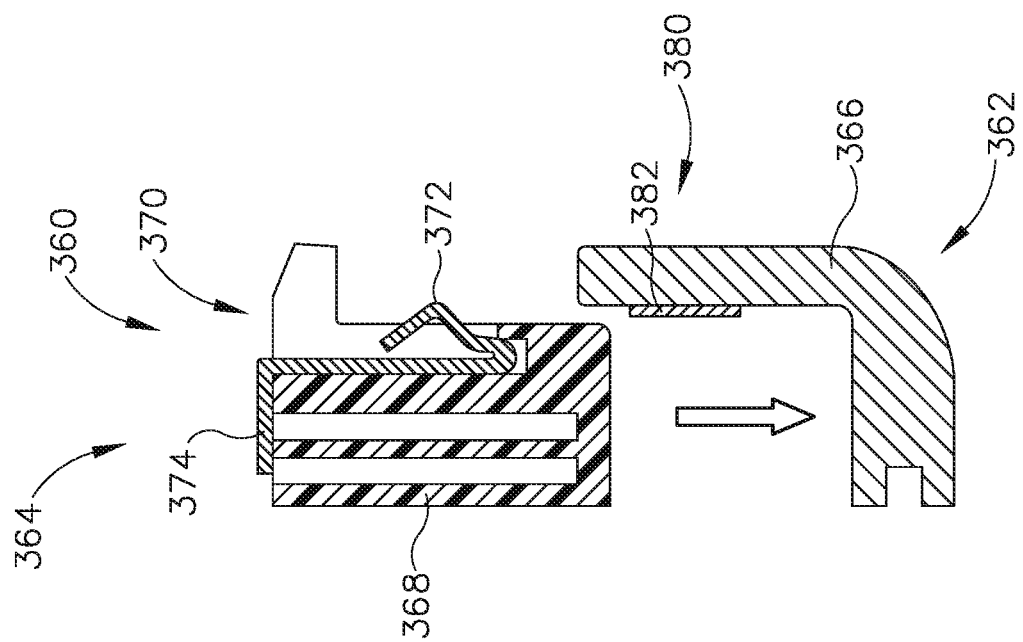

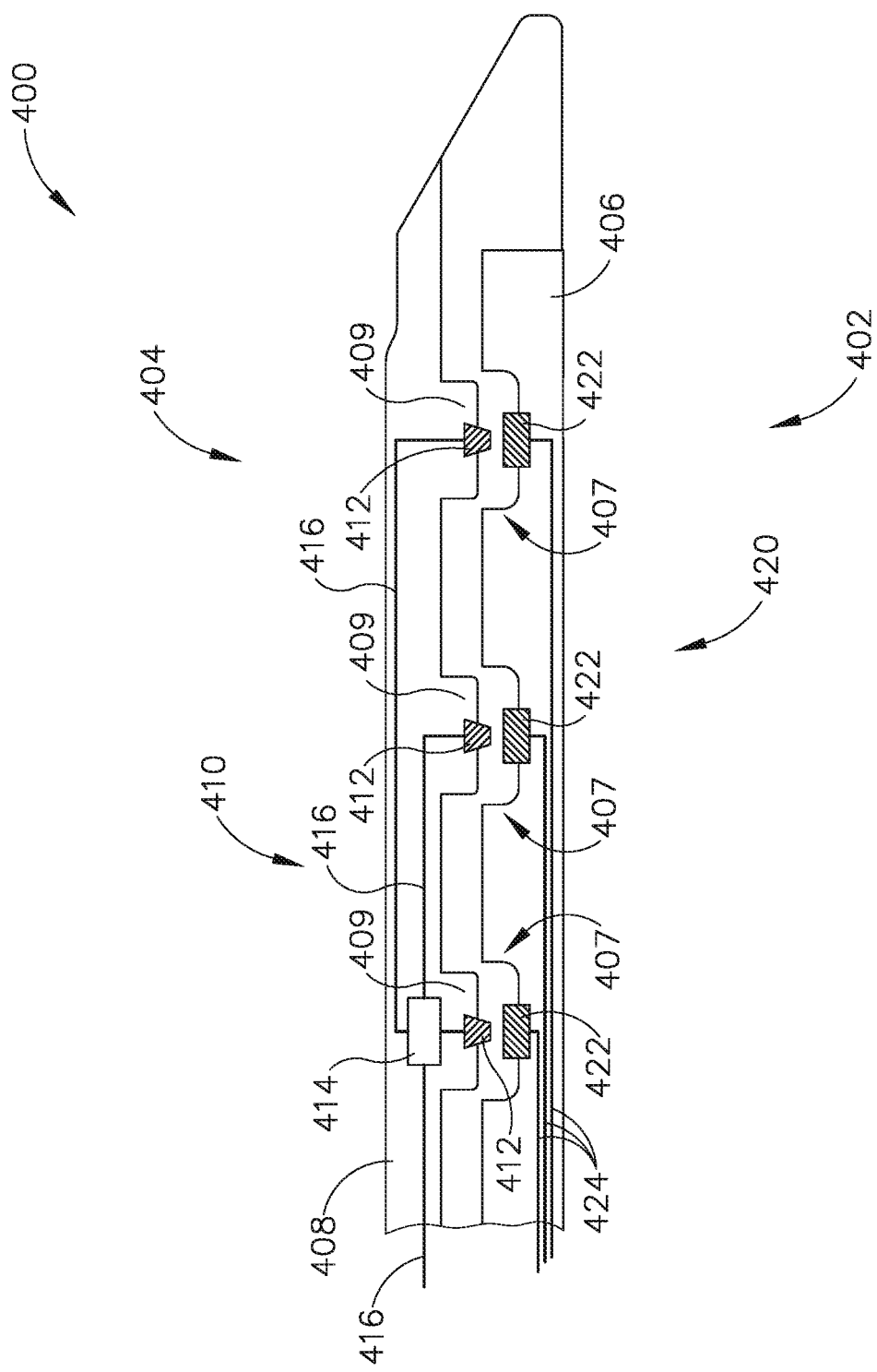

STAPLE CARTRIDGE WITH SHORT CIRCUIT PREVENTION FEATURES

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a top plan view of an exemplary channel contact assembly that may be readily incorporated into the end effector of FIG. 8;

FIG. 11 depicts a cross-sectional side view of an alternative cartridge and channel assembly that may be readily incorporated into the end effector of FIG. 8, where the cartridge is decoupled from the channel;

FIG. 17A depicts a cross-sectional end view of a portion of the cartridge and channel assembly of FIG. 16, where the cartridge is decoupled from the channel;

FIG. 17B depicts a cross-sectional end view of the portion of the cartridge and channel assembly of FIG. 16, where the cartridge is coupled with the channel;

FIG. 22A depicts a cross-sectional end view of a portion of the cartridge and channel assembly of FIG. 21, where the cartridge is decoupled from the channel;

FIG. 22B depicts a cross-sectional end view of the portion of the cartridge and channel assembly of FIG. 21, where the cartridge is coupled with the channel;

FIG. 23 depicts a cross-sectional side view of an alternative cartridge and channel assembly that may be readily incorporated into the end effector of FIG. 8;

Figure 1:
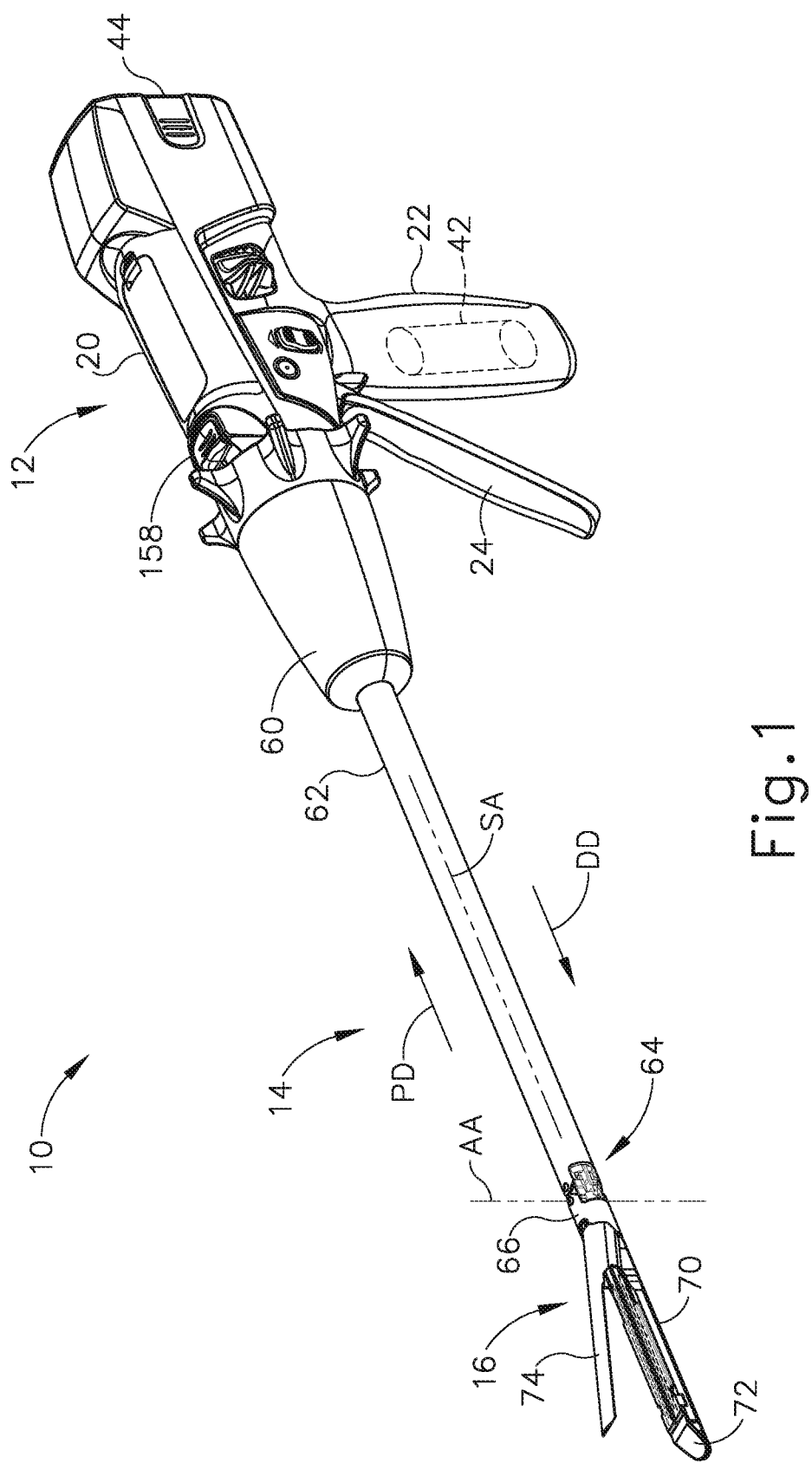
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Stapling Instrument

Figure 2:
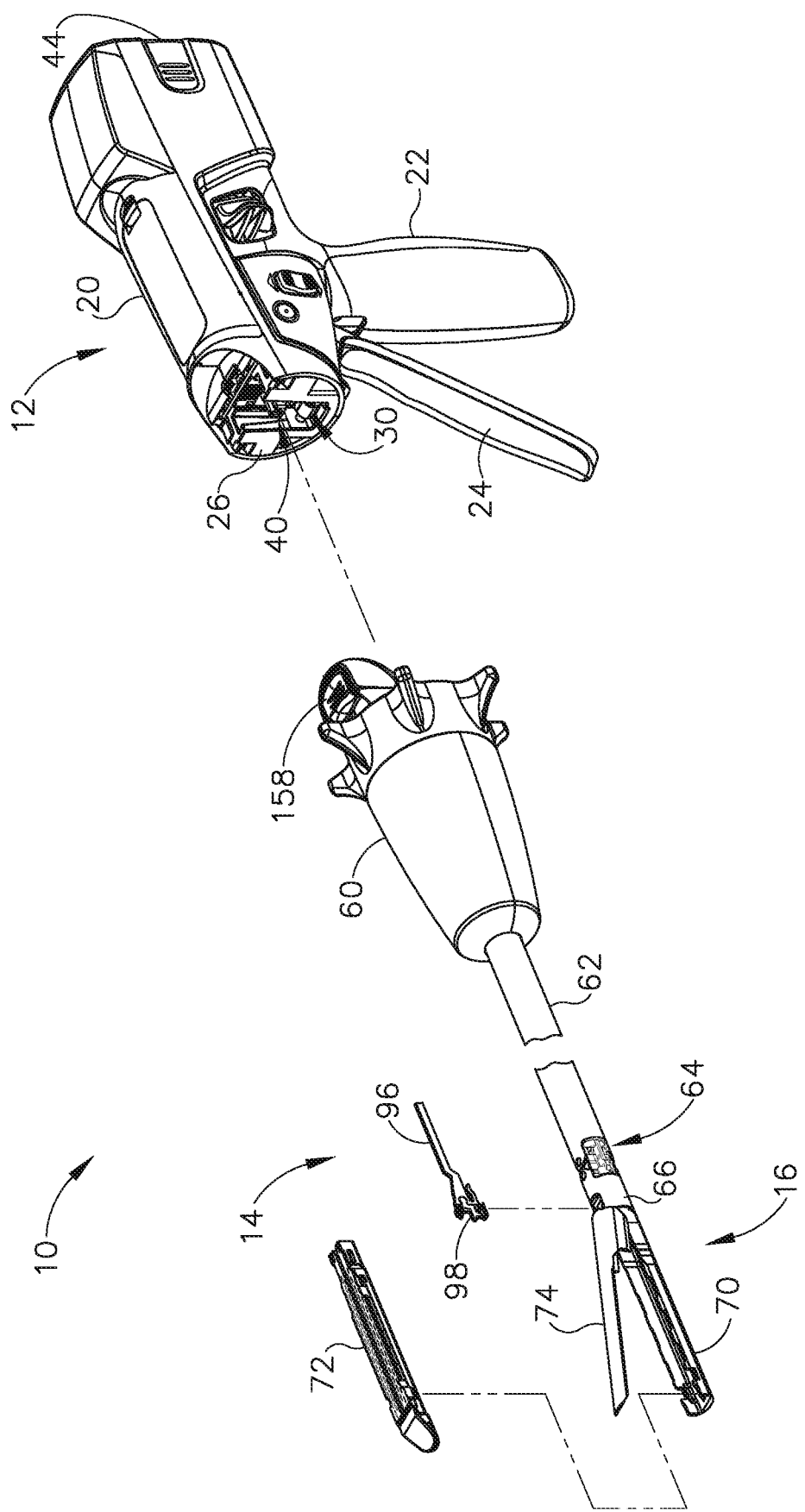
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
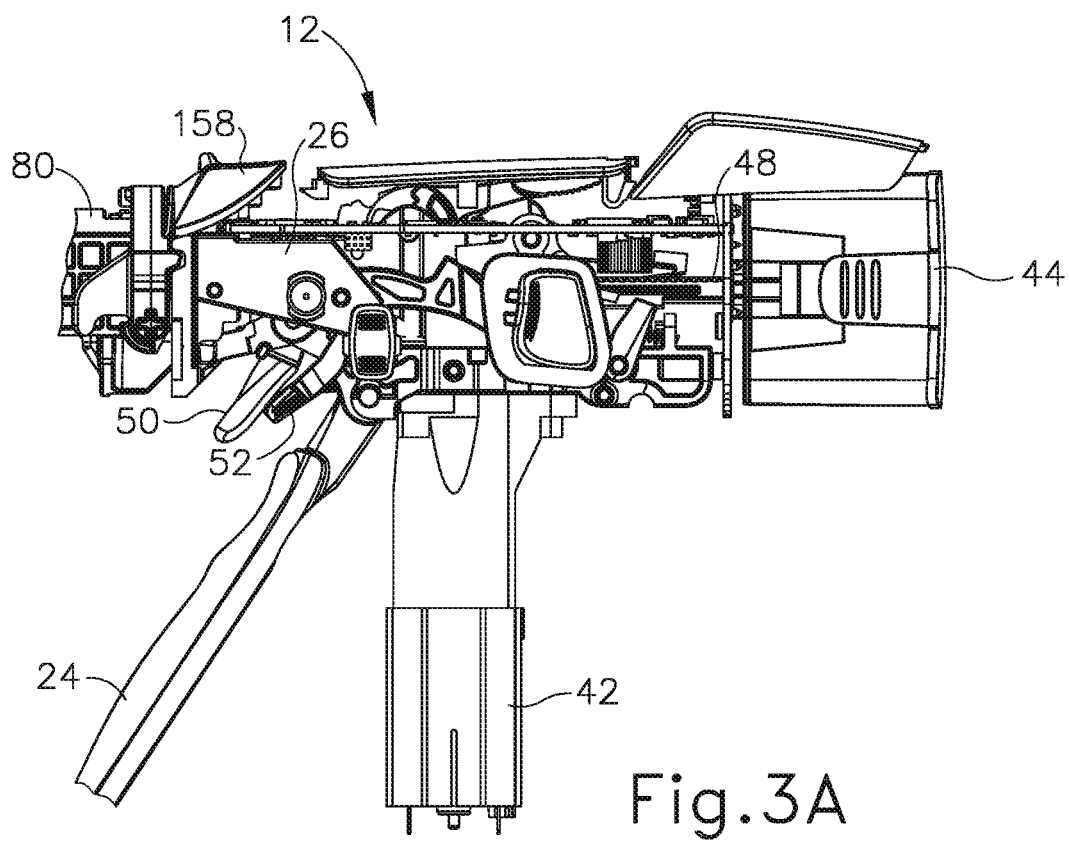
FIG. 3A depicts a side elevational view of the surgical instrument of FIG. 1, with a body of the handle assembly omitted, showing a closure trigger of the handle assembly in an unactuated position.
Figure 3B:
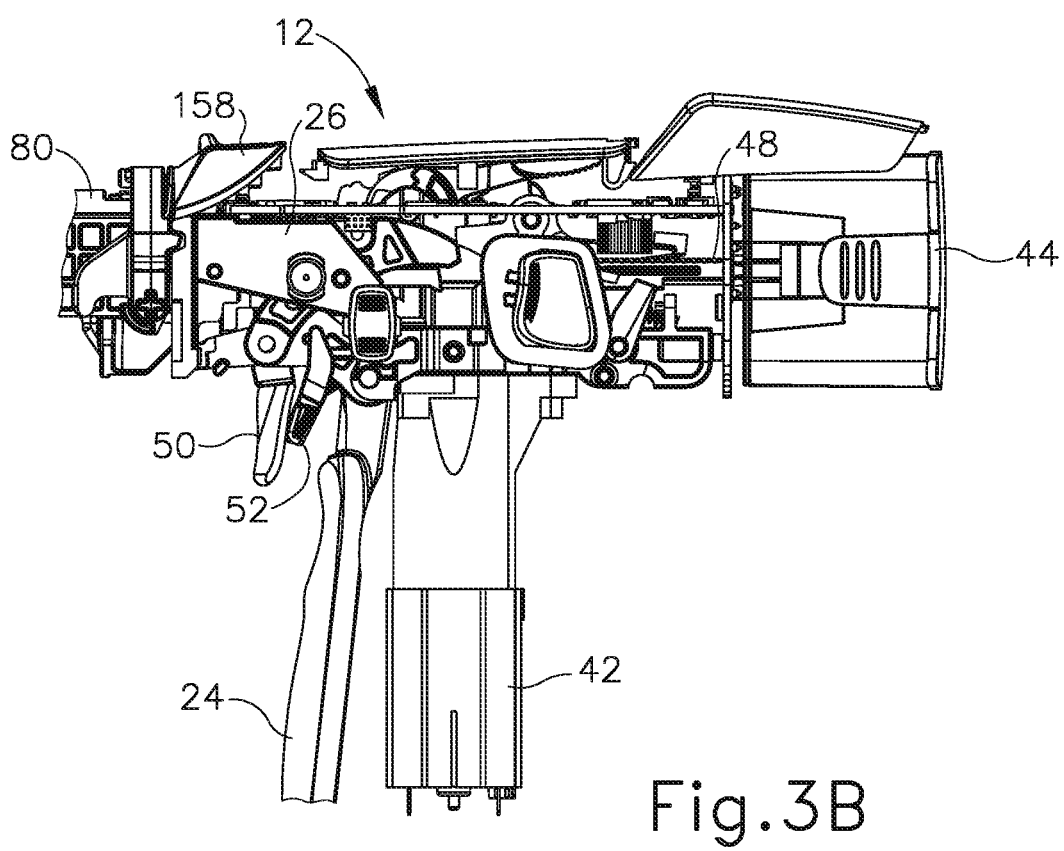
FIG. 3B depicts a side elevational view of the surgical instrument of FIG. 1, with a body of the handle assembly omitted, showing a closure trigger of the handle assembly in an actuated position.
Figure 4:
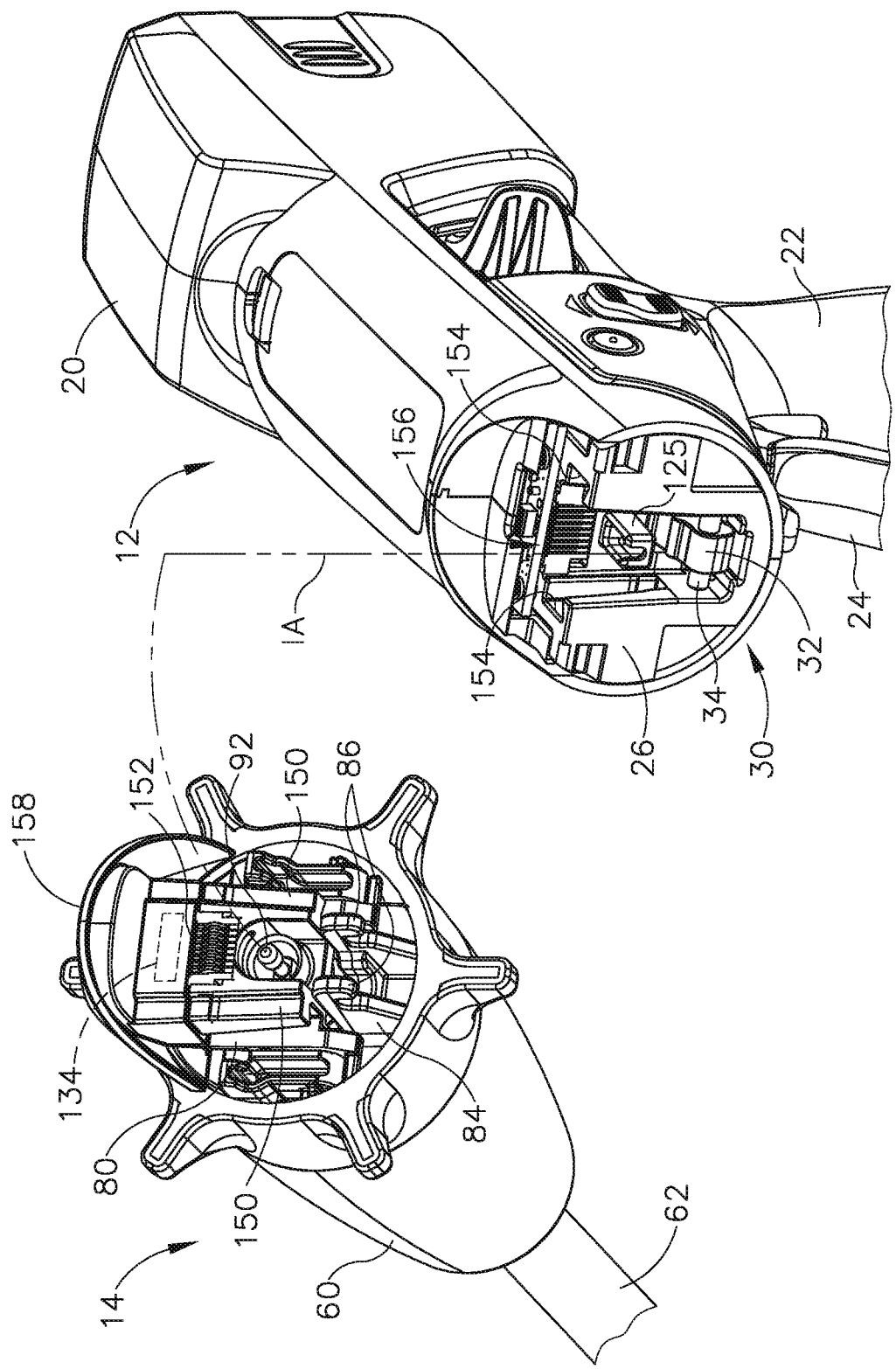
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
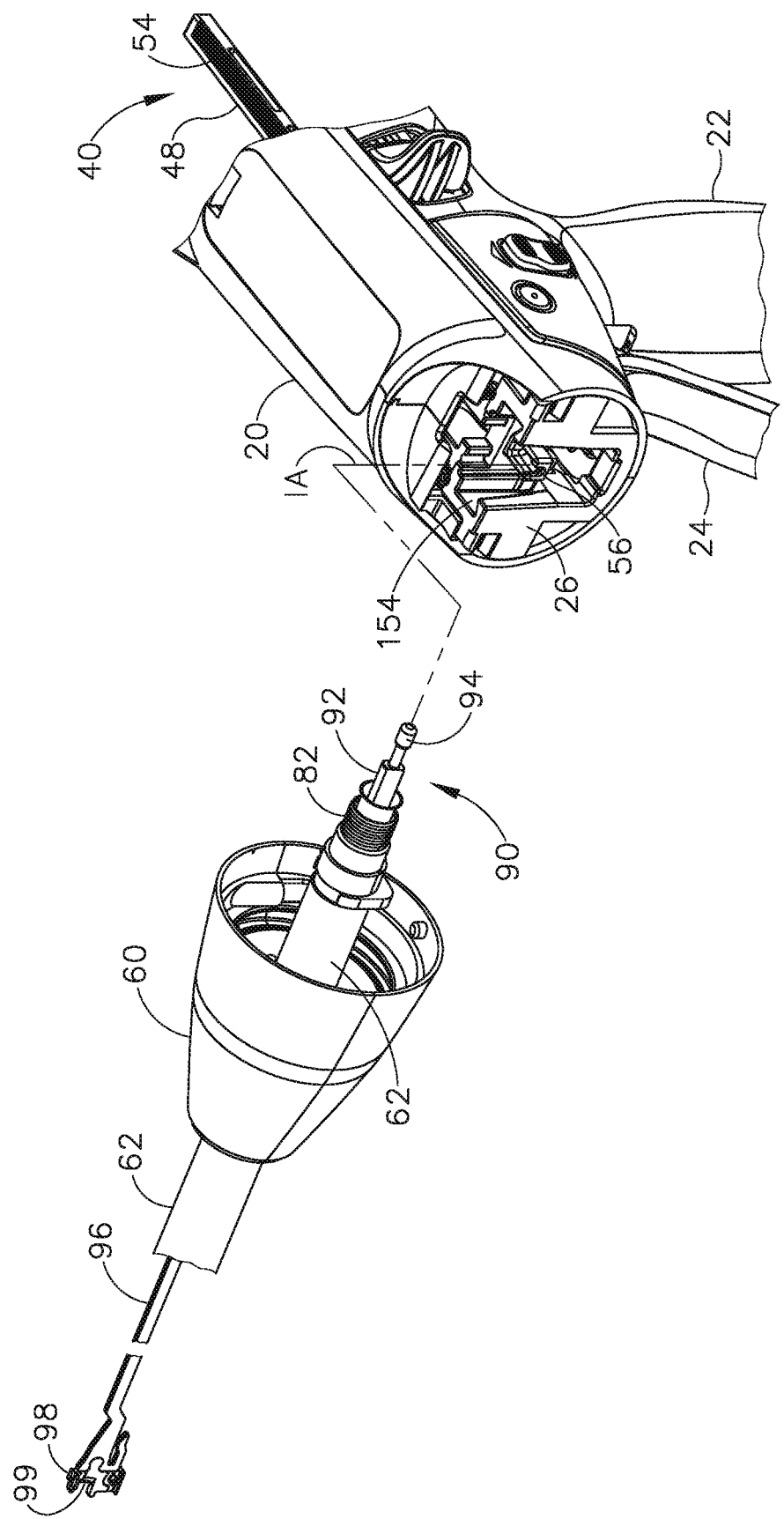
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. application Ser. No. 15/636,096, entitled "Surgical System Couplable With Staple Cartridge And Radio Frequency Cartridge, And Method Of Using Same," filed Jun. 28, 2017, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
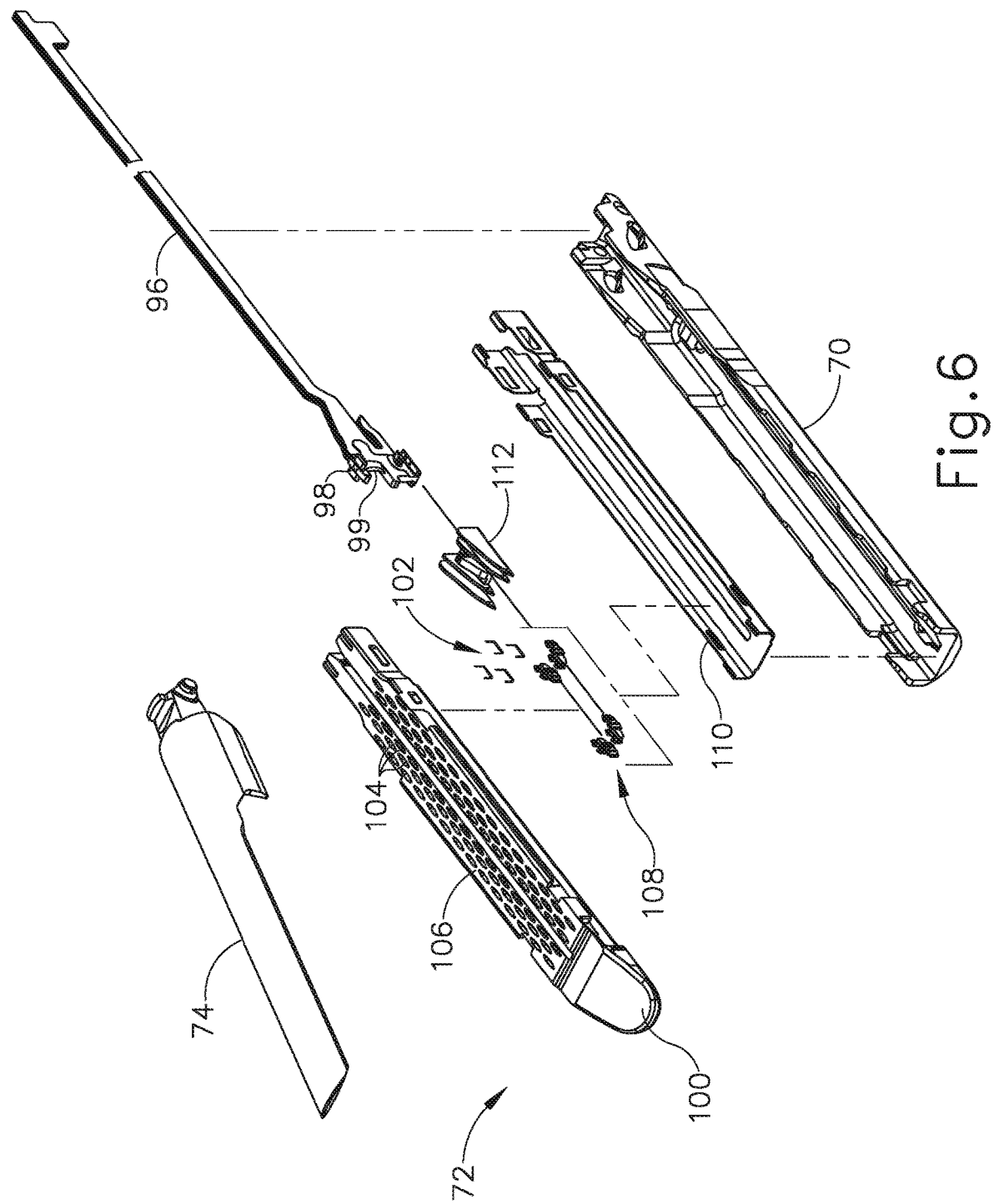
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
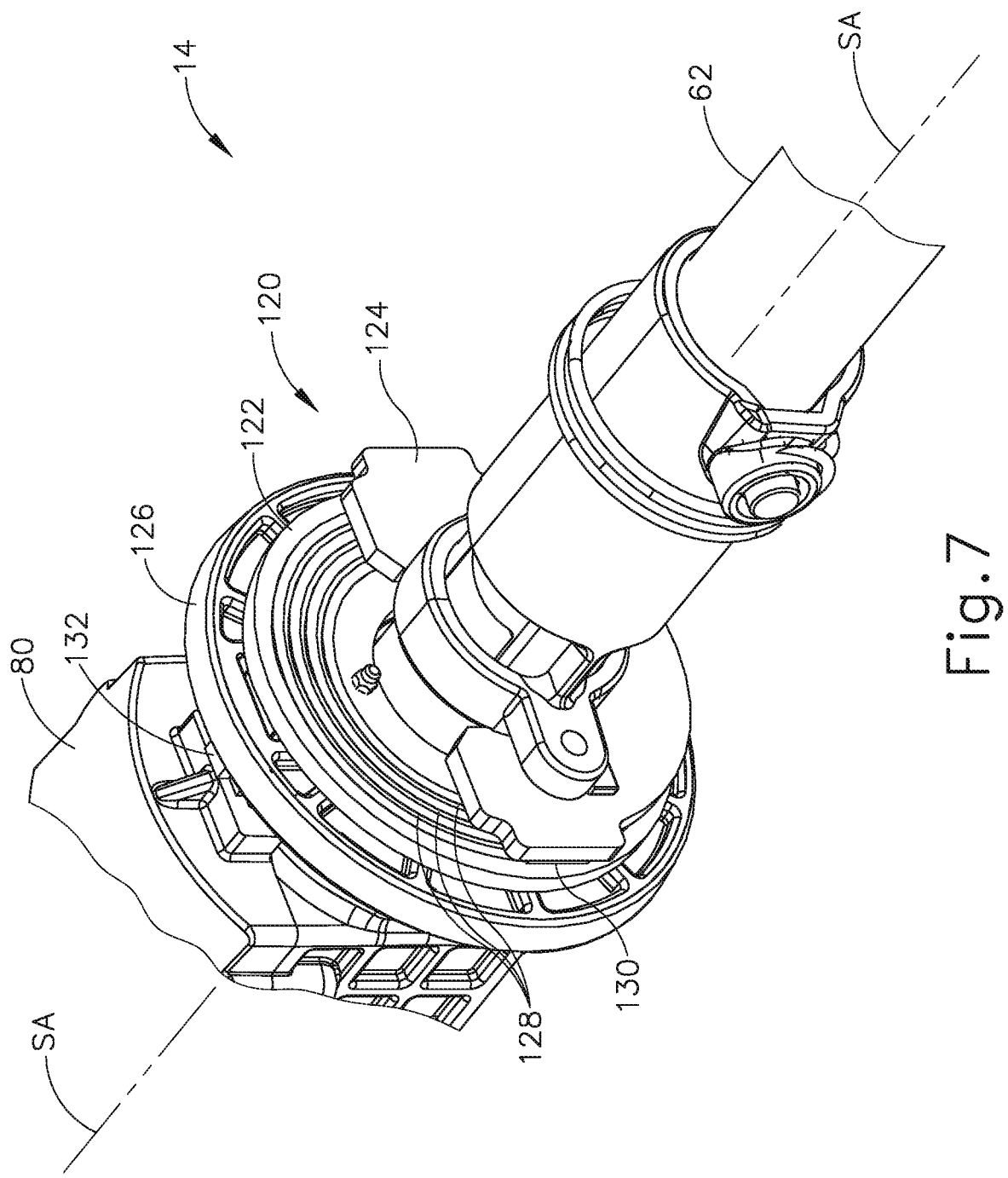
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) further includes a slip ring assembly (120) housed within nozzle (60) and configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122) about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156) when handle assembly (12) and interchangeable shaft assembly (14) are suitably coupled in accordance with the teachings herein. The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. application Ser. No. 15/635,663, entitled "Method For Articulating A Surgical Instrument," filed Jun. 28, 2017; U.S. application Ser. No. 15/635,631, entitled "Surgical Instrument With Axially Moveable Closure Member," filed Jun. 28, 2017; U.S. application Ser. No. 15/635,837, entitled "Surgical Instrument Comprising An Articulation System Lockable To A Frame," filed Jun. 28, 2017; U.S. Pat. Pub. No. 2016/0066911, entitled "Smart Cartridge Wake Up Operation And Data Retention," published Mar. 10, 2016; U.S. Pat. Pub. No. 2015/0272575, entitled "Surgical Instrument Comprising A Sensor System," published Oct. 1, 2015; U.S. Pat. Pub. No. 2014/0263552, entitled "Staple Cartridge Tissue Thickness Sensor System," published Sep. 18, 2014; and/or U.S. Pat. Pub. No. 2014/0263541, entitled "Articulatable Surgical Instrument Comprising An Articulation Lock," published Sep. 18, 2014, the disclosures of which are incorporated by reference herein.

E. Exemplary End Effector with Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
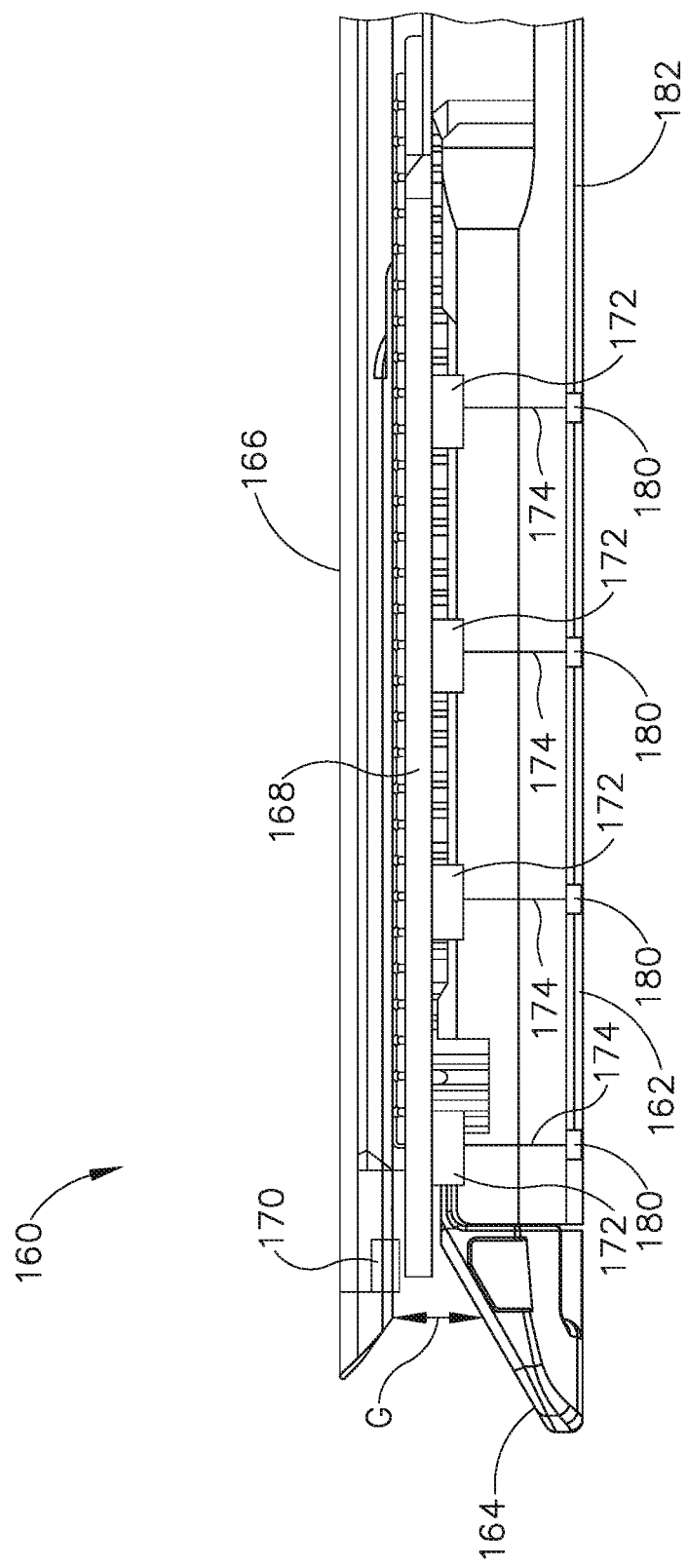
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, sensors (172) associated with staple cartridge (164) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

While sensors (172) are attached to staple cartridge (164) in the present example, any other type of electrically activated components may be used in addition to, or in replacement of, sensors (172). For example, one or more sensors (172) may be replaced with one or more elements designed to deliver electrical therapeutic energy to tissue captured within end effector (160), such as a pad that transmits Radio Frequency (RF) energy to tissue.

II. Cartridges and Channels with Alternative Electrical Contacts

As mentioned above, second sensors (172) associated with staple cartridge (164) are configured to couple with shaft circuit board (134) via contacts (174, 180) and electrical tracing (182) when staple cartridge (164) is suitably coupled with channel (162). As also mentioned above, shaft circuit board (134) may be powered by power pack (44) when interchangeable shaft assembly (14) is suitably coupled with handle assembly (12) in accordance with the description above. Therefore, when handle assembly (12) and interchangeable shaft assembly (14) are suitably coupled while power pack (44) is powering handle assembly (12), power pack (44) is also in electrical communication with contacts (180) located along channel (162).

As also mentioned above, staple cartridge (164) is dimensioned to selectively couple with channel (162) such that a first staple cartridge (164) may be used in accordance with the teachings herein, then be removed from channel (162), and then be replaced with an unused, second staple cartridge (164). Between removing a first staple cartridge (164) from channel (162) and coupling a second staple cartridge (164) with channel (162), an operator may dip the distal end of shaft assembly (14), including channel (162), into a saline solution to clean shaft assembly (14) for another use during the same surgical procedure. Additionally, during exemplary use, bodily fluids may accumulate within channel (162) and cartridge (164). Accumulation of saline solutions or bodily fluids may interfere with the electrical connection between corresponding contacts (174, 180), adversely affecting the electrical connection between corresponding contacts (174, 180). Additionally, accumulation of saline solutions or bodily fluids may interfere with specific contacts (174, 180), creating an undesirable short circuit.

It may therefore be desirable to provide a cartridge and/or channel assembly that may help prevent undesirable short circuits or other interferences with electrical connections (174, 180) via exposure to various fluids. While various examples of cartridges and channels are described below, it should be understood various combinations or modifications may be made to such cartridges and channels as would be apparent to one having ordinary skill in the art in view of the teachings herein.

Figure 9:
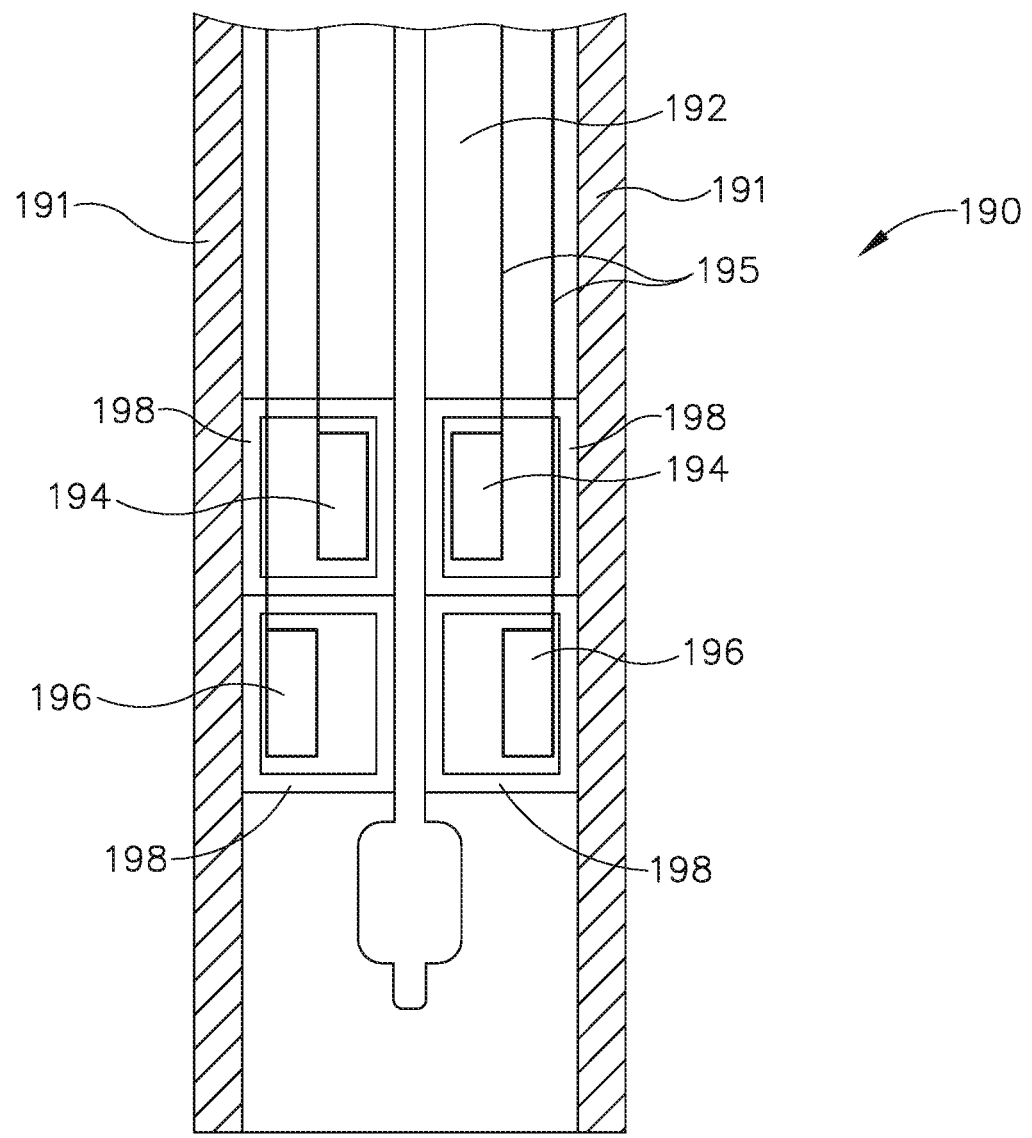
FIG. 9 depicts a top plan view of an alternative channel that may be readily incorporated into the end effector of FIG. 8.

FIG. 9 shows an exemplary alternative elongate channel (190) that may be readily incorporated into end effector (160) described above in replacement of elongate channel (162). Elongate channel (190) includes a base wall (192), two side walls (191), two hot contacts (194) and two return contacts (196) attached to an interior surface of base wall (192), a plurality of electrical traces/leads (195) extending from contacts (194, 196) to shaft circuit board (134), a hydrophobic perimeter (198). Because electrical traces/lead (195) extend from contacts (194, 196) to shaft circuit board (134), power pack (44) may electrically activate contacts (194, 196) when shaft assembly (14) is suitably coupled to handle assembly (12).

As will be described in greater detail below, hydrophobic perimeter (198) is configured to at least partially fluidly isolate individual contacts (194, 196) relative to each other in order to help prevent accumulated fluid from potentially creating a short circuit.

Each contact (194, 196) is configured to couple with a corresponding electrical contact (174) of cartridge (164). In particular, one hot contact (194) and one return contact (196) may each couple with an electrical contact (174) of cartridge (164) that are both in communication with electrically activated device (172). Therefore, when cartridge (164) is suitably coupled with elongate channel (190), electrically activated component (174) and corresponding electrical contacts (174) help complete a circuit between hot contact (194) and corresponding return contact (196).

As mentioned above, fluid may accumulate within the confines of elongate channel (190) on the interior surface of base wall (192). If accumulated fluid spans across base wall (192) to connect hot contact (194) with its corresponding return contact (196), the accumulated fluid may bridge a short circuit connection between corresponding contacts (194, 196). However, hydrophobic perimeter (198) surrounds each individual contact (194, 196). Hydrophobic perimeter (198) is made out of a material that repels fluidic substances from contact with perimeter (198). Therefore, Hydrophobic perimeter (198) acts as a fluidic barrier between contacts (194, 196). The fluidic barrier created by hydrophobic perimeter (198) may prevent accumulated fluid from spanning across corresponding hot contacts (194) and return contacts (196), thereby reducing the chance of fluid forming a short circuit.

In the current example, hydrophobic perimeter (198) individually encompasses each electrical contact (194, 196). However, hydrophobic perimeter (198) may encompass electrical contacts (194, 196) such that only corresponding contacts (194, 196) that may potentially form a short circuit are isolated from each other. Of course, any other suitable geometrical arrangement of hydrophobic perimeter (198) may be utilized as would be apparent to one having ordinary skill in the art in view of teachings herein. In the current example, two hot contacts (194) and two corresponding return contacts (196) are used. However, any suitable number of contacts (194, 196) may be used as would be apparent to one having ordinary skill in the art in view of the teachings herein.

FIGS. 10-11 show an exemplary alternative cartridge and channel assembly (200) that may be readily incorporated into end effector (160) in replacement of cartridge (164) and channel (162), as described above, respectively. Cartridge and channel assembly (200) include an elongate channel (202) and a staple cartridge (204). Channel (202) and cartridge (204) are substantially similar to channel (162) and cartridge (164) as described above, respectively, with differences elaborated below.

Staple cartridge (204) includes a cartridge body (208), and a cartridge contact assembly (210). An electrical contact (212) of cartridge contact assembly (210) is located on the underside of cartridge body (208)) in order to suitably couple with channel contact assembly (220). Cartridge contact assembly (210) also includes an electrically activated component (214) and a connector (216). Connector (216) establishes electrical communication between electrically activated component (214) and electrical contact (212).

Elongate channel (202) includes a channel body (206) and a channel contact assembly (220). Channel contact assembly (220) includes an electrical contact (222) and an O-ring (224). While not specifically shown, channel contact assembly (220) includes an electrical trace/lead (not shown) extending from electrical contact (222) to shaft circuit board (134). Because electrical trace/lead (not shown) extends from electrical contact (222) to shaft circuit board (134), power pack (44) may power electrical contact (222) when shaft assembly (14) is suitably coupled with handle assembly (12). While one contact each (212, 222) is shown, it should be understood that numerous contacts (212, 222) may be used, and any suitable number of contacts (212, 222) may be utilized as would be apparent to one having ordinary skill in the art in view of the teachings herein. For instance, a hot contact (222) and a return contact (222) may be located on channel (202) with a corresponding number of contacts (212) on cartridge (204).

O-ring (224) encompasses the perimeter of electrical contact (222) while also defining an opening (226). Electrical contact (222) is operable to electrically couple with contact (212) when cartridge (204) is suitably coupled with channel (202) via opening (226). Similar to hydrophobic perimeter (198), O-ring (224) acts as a fluidic barrier between contacts (222) on channel body (206) that would form a short circuit if fluid were to connect corresponding contacts (222). The fluidic barrier created by O-ring (224) may prevent accumulated fluid from spanning across corresponding hot contacts (222) and return contacts (222), thereby reducing the chance of fluid forming a short circuit.

FIG. 13A-13B show another exemplary channel and cartridge assembly (230) that may be readily incorporated into end effector (160) in replacement of cartridge (164) and channel (162), as described above, respectively. Cartridge and channel assembly (230) includes an elongate channel (232) and a staple cartridge (234). Elongate channel (232) and staple cartridge (234) are substantially similar to elongate channel (162) and staple cartridge (164) described above, with differences elaborated below. FIG. 10A shows cartridge (234) decoupled from channel (202); while FIG. 10B shows cartridge (234) coupled with channel (232).

Figure 12:
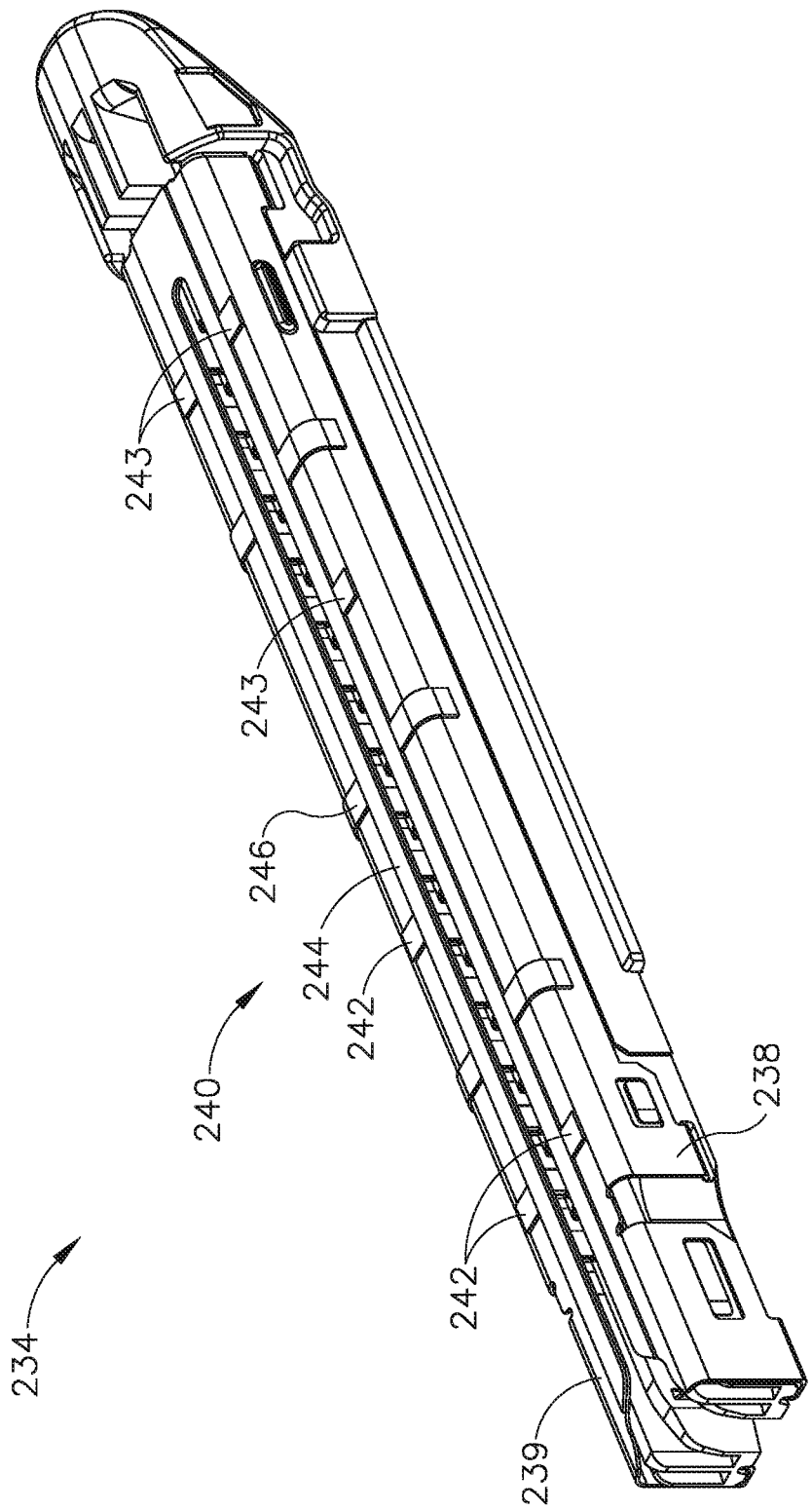
FIG. 12 depicts a perspective view of an alternative cartridge that may be readily incorporated into the end effector of FIG. 8.

Channel (232) includes a channel body (236) and a channel contact assembly (250). Channel body (232) defines a pair of lateral recesses (235) and a central recess (237). Channel contact assembly (250) includes contacts (252) housed within lateral recesses (235). Channel contact assembly (250) includes any suitable number of contacts (252) as would be apparent to one having ordinary skill in the art in view of the teachings herein. In the current example, channel contact assembly (250) includes six contacts (252), one for each contact (242, 243) on cartridge (234), as shown in FIG. 12. While not specifically shown, channel contact assembly (250) includes an electrical trace/lead (not shown) extending from electrical contact (252) to shaft circuit board (134). Because electrical trace/lead (not shown) extends from electrical contact (252) to shaft circuit board (134), power pack (44) may power electrical contact (252) when shaft assembly (14) is suitably coupled with handle assembly (12).

Figure 13:
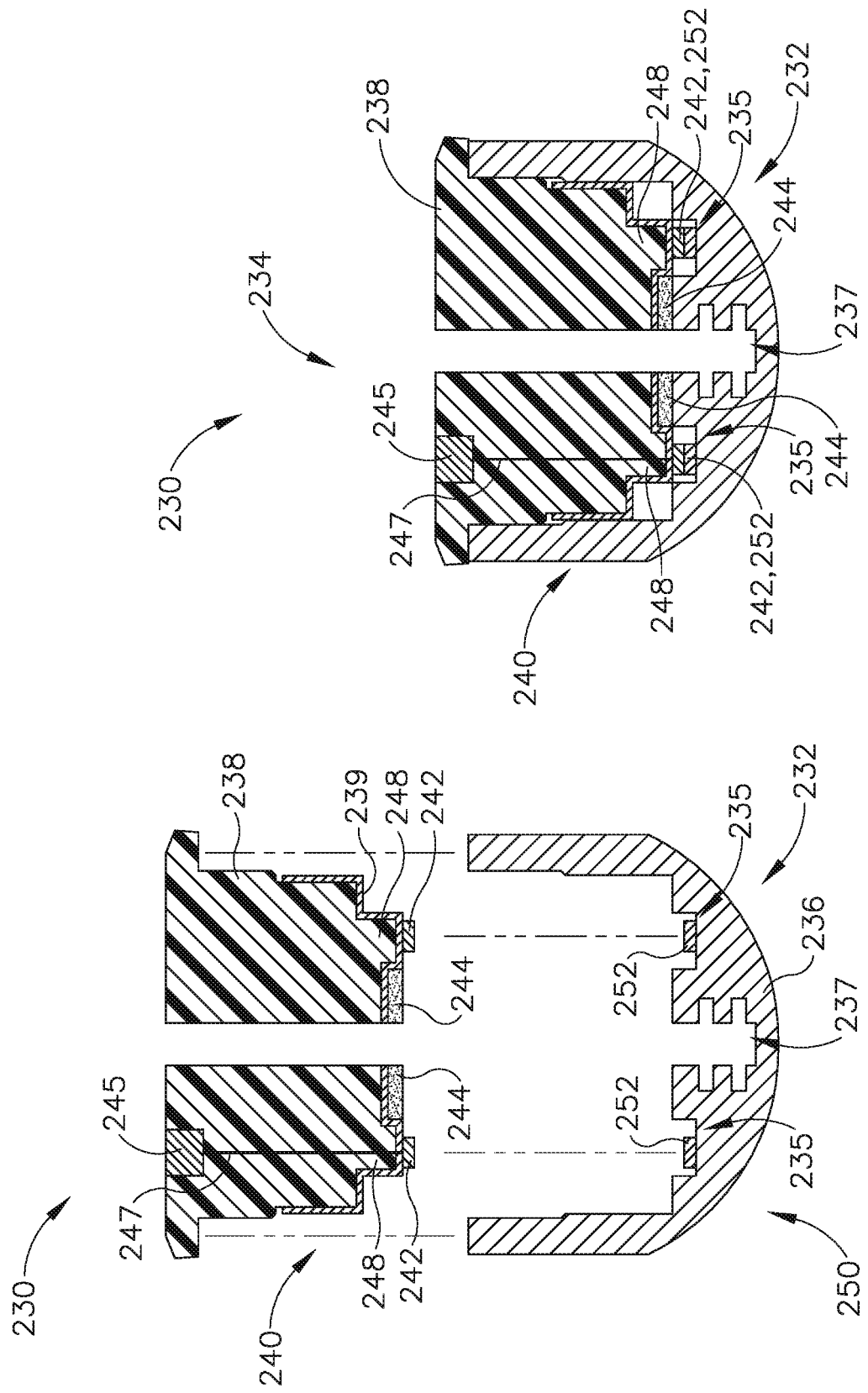
FIG. 13A depicts a cross-sectional end view of the cartridge of FIG. 12 and an alternative channel that may be readily incorporated into the end effector of FIG. 8, where the cartridge is decoupled from the channel.
FIG. 13B depicts a cross-sectional end view of the cartridge of FIG. 12 and the channel of FIG. 13, where the cartridge is coupled with the channel.

As best seen in FIGS. 12-13B, staple cartridge (234) includes a cartridge body (238) and a cartridge contact assembly (240). Cartridge body (238) includes a base portion (239). Cartridge contact assembly (240) includes a plurality of hot contacts (242), a plurality of return contacts (243), a longitudinally extending hydrophobic layer (144), various laterally extending hydrophobic layers (146), a plurality of electrically activated components (245), and a plurality of connectors (247).

Hot contacts (242) and return contacts (243) are disposed on base portion (239) of cartridge body (238). Hot contacts (242) and return contacts (243) are configured to couple with corresponding contacts (252) of channel contact assembly (250) when cartridge (234) is suitably coupled with channel (232). In particular, one hot contact (242) and one return contact (243) may be in electrical communication with the same electrically activated component (245). Therefore, when cartridge (234) is suitably coupled with elongate channel (232), electrically activated component (245) and corresponding electrical hot contacts (242) and return contacts (243) help complete a circuit between corresponding electrical contacts (252) of channel contact assembly (250).

Hot contacts (242) may be spaced away from return contacts (243) a sufficient distance along the longitudinal profile of base portion (239) such that it is difficult for a continuous portion of fluid to bridge a corresponding hot contact (242) and return contact (243) to create a short circuit. In other words, corresponding contacts (242, 243) are sufficiently spaced from each other in order to reduce the likelihood fluid will create a short circuit across contacts (242, 243). Since contact (252) on channel (232) are dimensioned to correspond with contacts (242, 243) on cartridge (234), it may also be difficult for fluid to span across corresponding contacts (252) to form a short circuit as well.

Additionally, hydrophobic layers (244, 246) surround each individual contact (194, 196). Hydrophobic layers (244, 246) are made out of a material that repels fluidic substances from contact with layers (244, 246). Therefore, Hydrophobic layers (244, 246) act as a fluidic barrier between contacts (242, 243). The fluidic barrier created by hydrophobic layers (244, 246) may prevent accumulated fluid from spanning across corresponding hot contacts (242) and return contacts (243), thereby reducing the chance of fluid forming a short circuit.

In the current example, hydrophobic layers (244, 246) individually encompasses each electrical contact (242, 243). However, hydrophobic layers (244, 246) may encompass electrical contacts (242, 243) such that only corresponding contacts (242, 243) that may potentially form a short circuit are isolated from each other. Of course, any other suitable geometrical arrangement of hydrophobic layers (244, 246) may be utilized as would be apparent to one having ordinary skill in the art in view of teachings herein. In the current example, three hot contacts (242) and two corresponding return contacts (243) are used. However, any suitable number of contacts (242, 243) may be used as would be apparent to one having ordinary skill in the art in view of the teachings herein.

Additionally, as mentioned above, and as will be described in greater detail below, channel body (236) defines both lateral recesses (235) and a central recess (237). Recesses (235, 237) may help create a difficult path for fluid to accumulate and short circuit corresponding electrical contacts (252) for hot contacts (242) and corresponding return contacts (243) when those contacts (252) are located laterally across central recess (237). Additionally, contacts (242, 243) are located on boss (248) of cartridge body (238). When contacts 9242, 243) couple with corresponding contacts (252) of channel (232), bosses (248) and contacts (242, 243) may force fluid accumulated within lateral recess (235) out or recesses (235) and away from the electrical connection formed by contacts (242, 243, 252).

Figure 14:
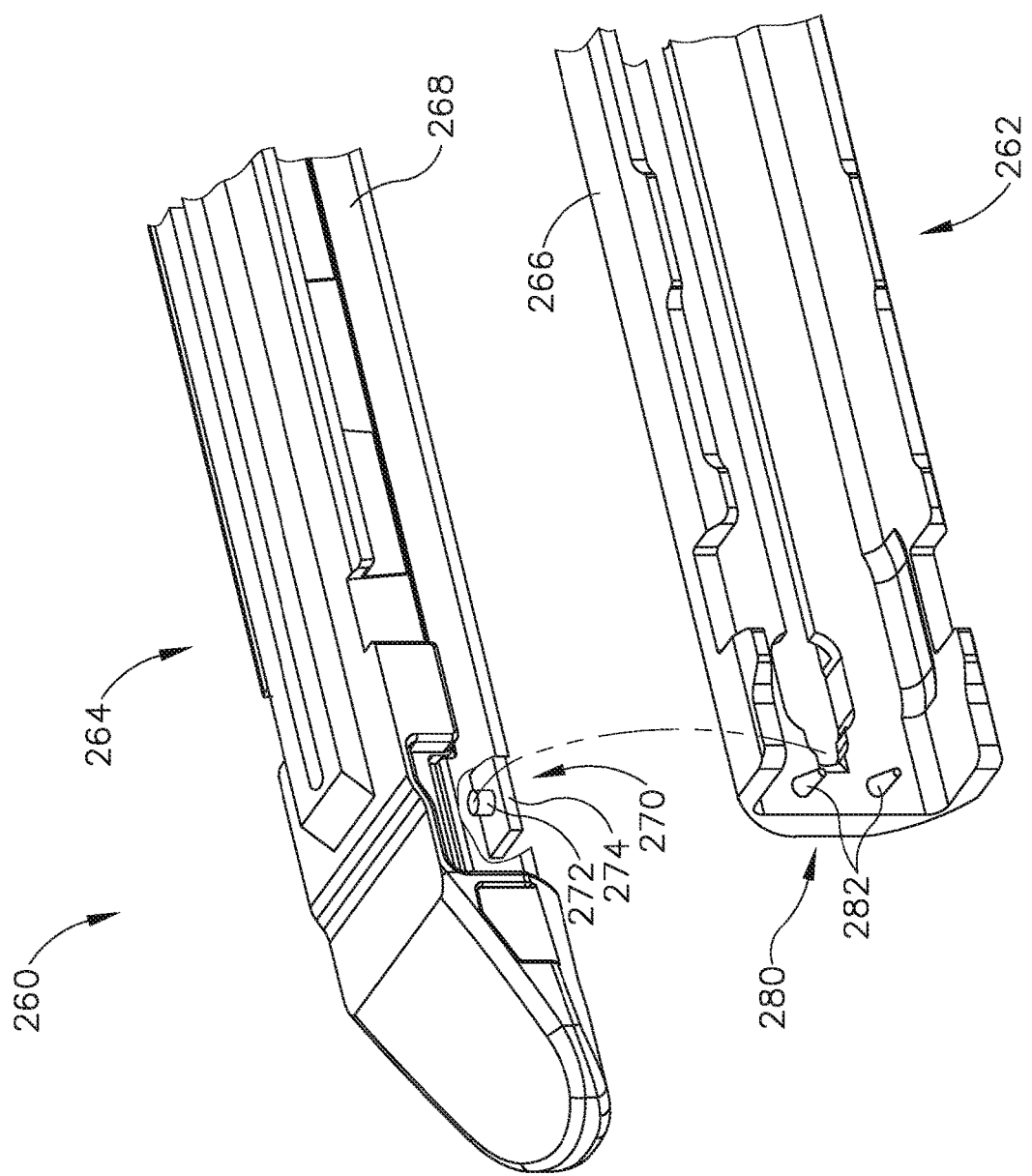
FIG. 14 depicts an exploded perspective view of an alternative cartridge and channel assembly that may be readily incorporated into the end effector of FIG. 8.
Figure 15:
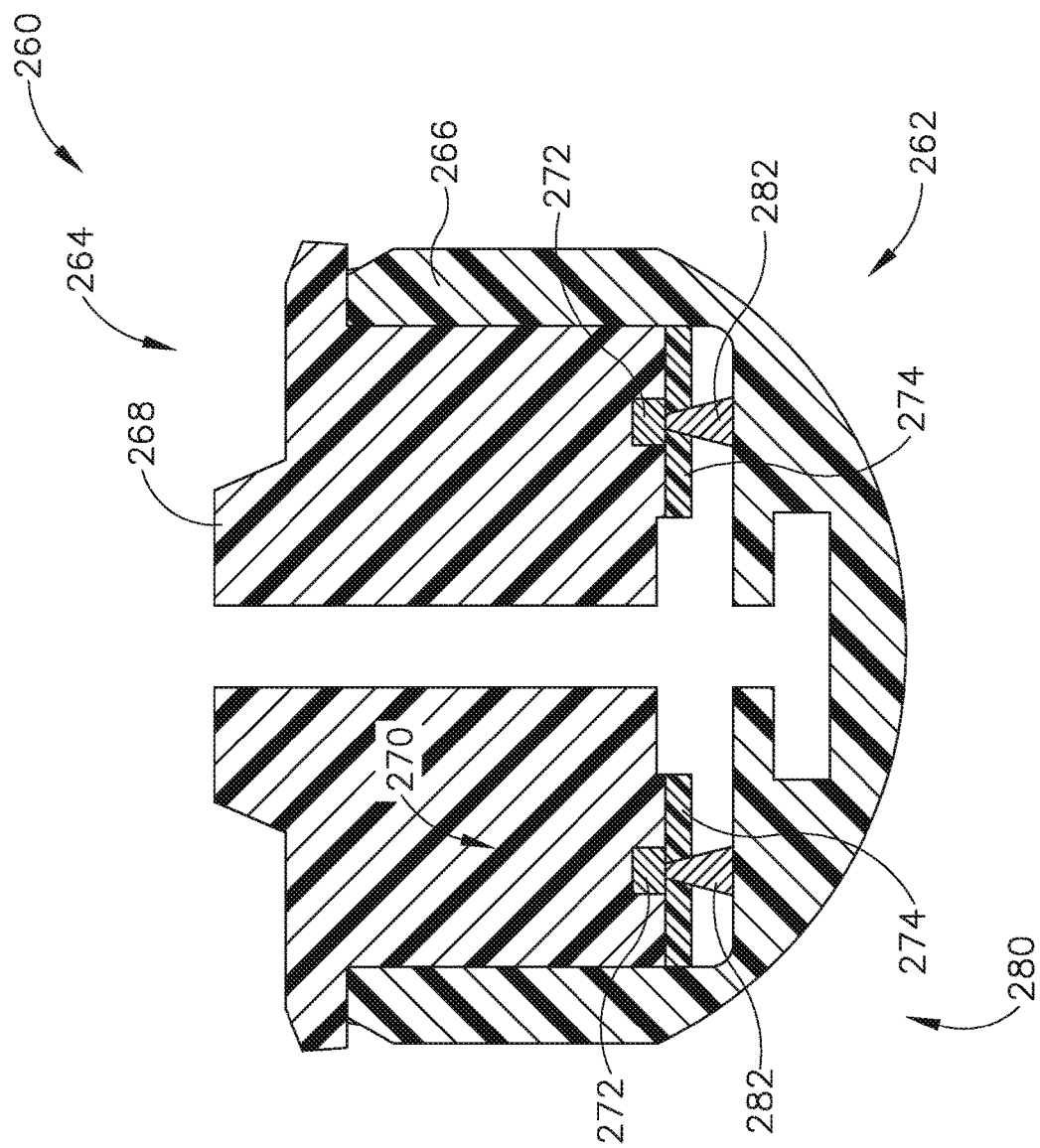
FIG. 15 depicts a cross-sectional view of the cartridge and channel assembly of FIG. 14.

FIGS. 14-15 show another exemplary alternative cartridge and channel assembly (260) that may be readily incorporated into end effector (160) in replacement of cartridge (164) and channel (162), as described above, respectively. Cartridge and channel assembly (260) includes an elongate channel (262) and a staple cartridge (264). Channel (262) and cartridge (264) are substantially similar to channel (162) and cartridge (164), as described above, respectively, with difference elaborated below. In particular, FIG. 14 shows cartridge (264) decoupled from channel (262); while FIG. 15 shows cartridge (264) coupled with channel (232).

Channel (262) includes a channel body (266) and a channel contact assembly (280). Channel contact assembly (280) includes any suitable number of contacts (282) as would be apparent to one having ordinary skill in the art in view of the teachings herein. In the current example, channel contact assembly (280) includes two contacts (282), one for each contact (272) on cartridge (264), as shown in FIG. 15. While not specifically shown, channel contact assembly (280) includes an electrical trace/lead (not shown) extending from electrical contact (282) to shaft circuit board (134). Because electrical trace/lead (not shown) extends from electrical contact (282) to shaft circuit board (134), power pack (44) may power electrical contact (282) when shaft assembly (14) is suitably coupled with handle assembly (12).

Cartridge (264) includes a cartridge body (268) and a cartridge contact assembly (270). Cartridge contact assembly (270) includes a pair of electrical contacts (272) each having a corresponding gasket member (274). While not shown, electrical contacts (272) are in electrical communication with an electrically activated component (not shown) such that one electrical contact (272) is a hot contact and the other electrical contact (272) is a return contact. As will be described in greater detail below, electrical contacts (272) are configured to electrically couple with contacts (282) of channel (262) such that power pack (44) may power electrically activated component (not shown) when shaft assembly (14) is suitably coupled with handle assembly (12).

Gasket members (274) are configured to transition between a closed state and an open state. Gasket members (274) protect electrical contacts (272) from exposure to outside fluids in both the close state and the open state. In particular, gasket members (274) allow electrical contacts (282) to couple with electrical contacts (272) in the open state. When cartridge (264) is no longer suitably coupled with channel (262), gasket members (274) transition into a closed stated. As best shown in FIG. 15, electrical contacts (282) protrude from an interior base surface of channel body (266). When cartridge (264) is suitably coupled with channel (262), electrical contacts (282) are configured to open up gasket members (274) in order to electrically couple with contacts (272). Gasket members (274) may make slide against contacts (282) during coupling of cartridge (264) with channel (262) such that fluid on contacts (282) is removed. Gasket member (274) may be sufficiently resilient such that when cartridge (264) is removed, gasket member (274) returns to a closed state in other to further protect electrical contacts (272) from exposure to outside fluids. Gasket members (274) may also be sufficiently resilient as to form a seal around contacts (282) when contacts (282, 272) are electrically coupled and gasket members (274) are in the opened state.

Figure 16:
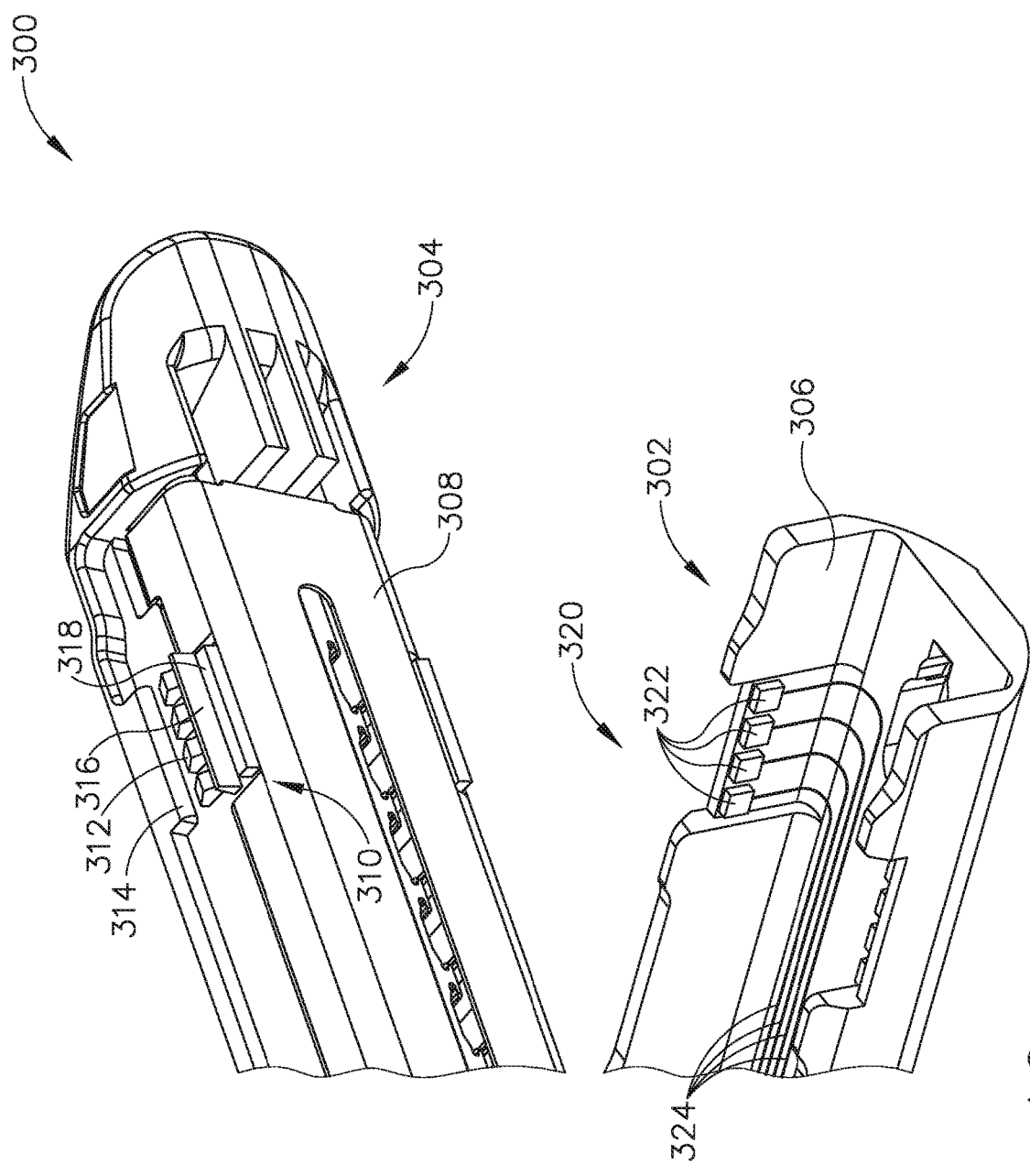
FIG. 16 depicts an exploded perspective view of an alternative cartridge and channel assembly that may be readily incorporated into the end effector of FIG. 8.

FIGS. 16-17B show another exemplary alternative cartridge channel assembly (300) that may be readily incorporated into end effector (160) in replacement of cartridge (164) and channel (162), as described above, respectively. Cartridge and channel assembly (300) includes an elongate channel (302) and a staple cartridge (304). Channel (302) and cartridge (304) are substantially similar to channel (162) and cartridge (164) described above, with differences elaborated below. FIG. 17A shows cartridge (304) decoupled from channel (302); while FIG. 17B shows cartridge (304) coupled with channel (302).

Channel (302) includes a channel body (306) and a channel contact assembly (320). Channel contact assembly (320) includes any suitable number of contacts (322) as would be apparent to one having ordinary skill in the art in view of the teachings herein. In the current example, channel contact assembly (320) includes eight contacts (322). Channel contact assembly (320) also includes an electrical trace/ lead (324) extending from electrical contacts (322) to shaft circuit board (134). Because electrical trace/lead (324) extends from electrical contact (322) to shaft circuit board (134), power pack (44) may power electrical contact (322) when shaft assembly (14) is suitably coupled with handle assembly (12).

Cartridge (304) includes a cartridge body (308) and a cartridge contact assembly (310). Cartridge contact assembly (310) includes a plurality of electrical contacts (312), a sealing portion (314), a wiper portion (316), and a sponge portion (318). While not shown, various electrical contacts (312) are in electrical communication with various electrically activated component (not shown) such that one electrical contact (312) is a hot contact and a second electrical contact (312) is a return contact. As shown in FIG. 17B, electrical contacts (312) are configured to electrically couple with contacts (322) of channel (302) such that power pack (44) may power electrically activated component (not shown) when shaft assembly (14) is suitably coupled with handle assembly (12). As will also be described in greater detail below, various portions of cartridge contact assembly (310) are configured to absorb fluid away from, wipe fluid away from, or prevent fluid from entering into contact with electrical contacts (312, 322) while cartridge (304) is either coupling with channel (302) or already suitably coupled with channel (302).

As best seen in FIG. 17A, wiper portion (316) is located directly adjacent to and underneath electrical contacts (312), while sponge portion (318) is located directly adjacent to an underneath wiper portion (316). If fluid (F) is present within the confines of channel body (306) near contacts (322), the act of inserting cartridge (304) into channel (302) encourages sponge portion (318) to absorb fluid (F) away from contacts (322) and wiper portion (316) to wipe fluid (F) away from contacts (322).

In particular, when cartridge (304) is initially inserted into channel (302), sponge portion (318) may make initial contact with the interior surface of channel body (306) supporting contacts (322). Sponge portion (318) is sufficiently resilient to deform in response to contact with the interior surface of channel body (306) so that sponge portion (318) may remain in contact with the interior surface of channel body (306) and contacts (322) without inhibiting the insertion of cartridge (304) into channel (302). Sponge portion (318) may absorb an amount of fluid (F) that accumulated within the confines of channel (302) during and after insertion of cartridge (304). Therefore, sponger portion (318) may help prevent fluid (F) from interfering with the electrical connection between contacts (312, 322).

When cartridge (304) is initially inserted into channel (302), wiper portion (316) may also make initial contact with the interior surface of channel body (306) supporting contacts (322). Wiper portion (316) is also sufficiently resilient to deform in response to contact with the interior surface of channel body (306) so that wiper portion (316) may remain in contact with the interior surface of channel body (306) and contacts (322) without inhibiting the insertion of cartridge (304) into channel (302). Wiper portion (316) is made of a sufficient material such that as wiper portion (316) is inserted, wiper portion (316) forces fluid (F) away from contact (322) and toward the base of channel body (306) such that sponge portion (318) may absorb fluid (F). Therefore, wiper portion (316) may help prevent fluid (F) from interfering with the electrical connection between contacts (312, 322).

Sealing portion (314) is located above contacts (312). As best seen in FIG. 17B, sealing portion (314) is dimensioned to abut against a top surface of channel body (306) when cartridge (304) is suitably coupled with channel (302). Sealing portion (314) abuts against channel body (306) in such a manner as to form a fluid tight seal, thereby helping prevent additional fluid (F) from entering into the interior of channel (302) and interfering with the electrical connection between contacts (312, 322) during exemplary use. While in the current example, sealing portion (314) is located above contacts (312), sealing portion (314) may be place at any suitable position relative to contacts (312) as would be apparent to one having ordinary skill in the art in view of the teachings herein. For example, sealing portion (314) may extend along the side portion of contacts (312) alternatively or addition to being located above contacts (312).

Figure 18A:
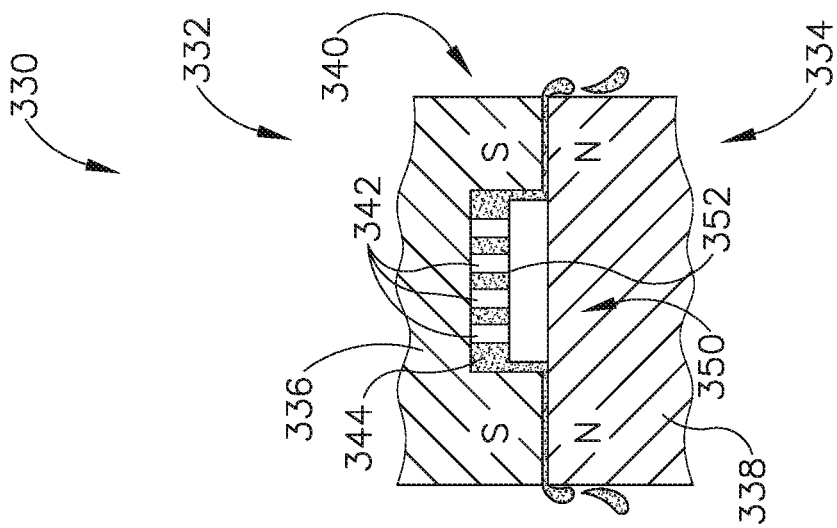
FIG. 18A depicts a cross-sectional end view of an alternative cartridge and channel assembly that may be readily incorporated into the end effector of FIG. 8, where the cartridge is decoupled from the channel.
Figure 18B:
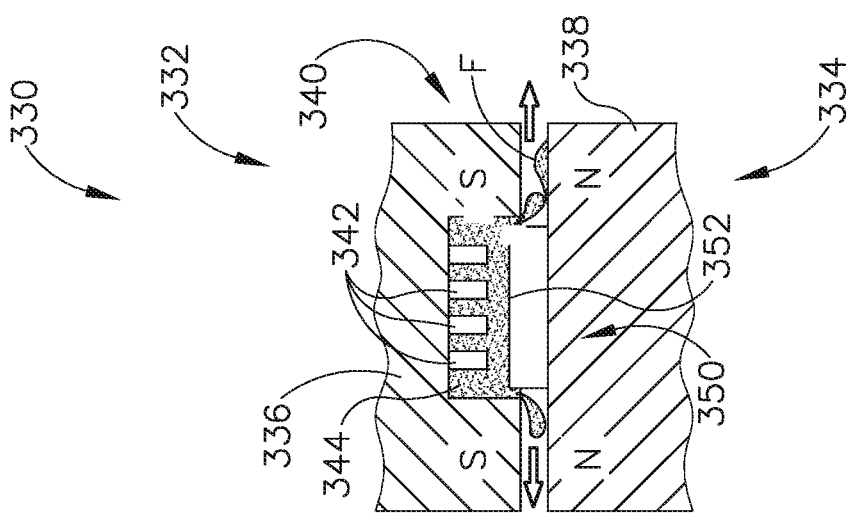
FIG. 18B depicts a cross-sectional end view of the cartridge and channel assembly of FIG. 18A, where the cartridge is partially coupled with the channel.
Figure 18C:
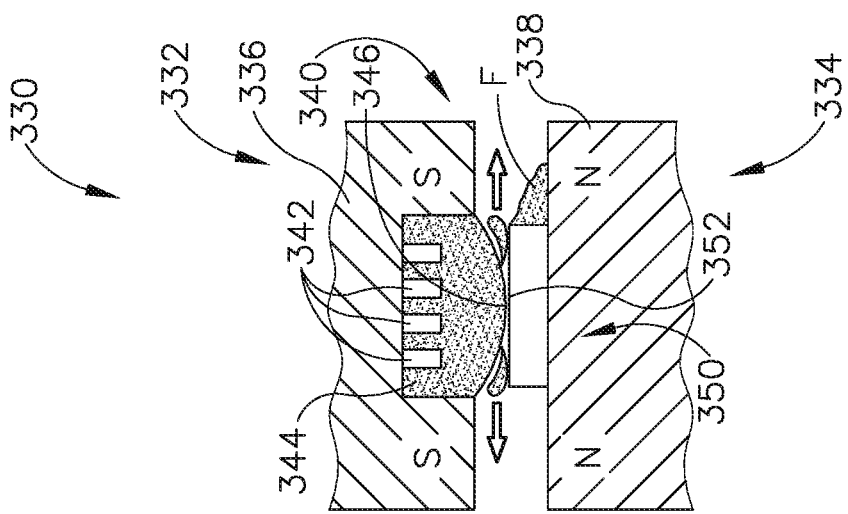
FIG. 18C depicts a cross-sectional end view of the cartridge and channel assembly of FIG. 18A, where the cartridge is fully coupled with the channel.

FIGS. 18A-18C show an alternative exemplary cartridge and channel assembly (330) that may be readily incorporated into end effector (160) in replacement of cartridge (164) and channel (162), as described above, respectively. Cartridge and channel assembly (330) include an elongate channel (332) and a staple cartridge (334). Channel (332) and cartridge (334) are substantially similar to channel (162) and cartridge (164) as described above, respectively, with differences elaborated below. FIG. 18A shows cartridge (334) decoupled from channel (332). FIG. 18B shows cartridge (334) partially coupled with channel (332), and FIG. 18C shows cartridge (334) fully coupled with channel (332).

Channel (332) includes a channel body (336) and a channel contact assembly (340). The portion of channel body (336) housing channel contact assembly (340) is magnetically charged. Channel contact assembly (340) includes a plurality of contacts (342) housed within a penetrable elastomeric cover (344). In the current example, channel contact assembly (340) includes four contacts (342). While not specifically shown, channel contact assembly (340) includes an electrical trace/lead (not shown) extending from electrical contacts (242) to shaft circuit board (134). Because electrical trace/lead (not shown) extends from electrical contacts (342) to shaft circuit board (134), power pack (44) may power electrical contact (342) when shaft assembly (14) is suitably coupled with handle assembly (12).

Cartridge (334) includes a cartridge body (338) and a cartridge contact assembly (350). The portion of cartridge body (338) housing cartridge contact assembly (350) is magnetically charged such that that portion of cartridge body (338) is magnetically attracted to the portion of channel body (336) housing channel contact assembly (340). Cartridge contact assembly (350) includes a plurality electrical contacts (352) configured to electrically couple with a corresponding electrical contact (342) of channel contact assembly (340). While not shown, electrical contacts (342) are in electrical communication with an electrically activated component (not shown) such that one electrical contact (342) is a hot contact and another electrical contact (342) is a return contact. As shown in FIG. 18C, electrical contacts (352) are configured to electrically couple with contacts (342) of channel (332) such that power pack (44) may power electrically activated component (not shown) when shaft assembly (14) is suitably coupled with handle assembly (12).

A mentioned above, channel contact assembly includes an elastomeric cover (344). Elastomeric cover (344) is attached to channel body (336) and houses electrical contacts (342). Elastomeric cover (344) includes a concave exterior surface (346). Elastomeric cover (344) is resiliently deformable from a relaxed position (as shown in FIG. 18A), to a deformed positioned (as shown in FIG. 18C). As best shown between FISG. 18A-18B, concave exterior surface (346) of cover (344) is configured to abut against electrical contacts (352) during initial insertion of cartridge (334) into channel (332). The geometric shape of concave exterior surface (346) is configured to forces accumulate fluid (F) associated with contacts (352) away from contacts (352). In other words, concave exterior surface (346) may help wipe away fluid from the electrical connection between contacts (342, 352). As best seen between FIGS. 18A-18B, due to the resilient nature of elastomeric cover (344), an operator may push cartridge (334) further toward channel (332) in order to deform cover (344). Additionally, concave exterior surface (346) of elastomeric cover (344) may be penetrated by contacts (342) under sufficient force such that contacts (342, 352) may electrically couple with each other. As mentioned above, bodies (336, 338) housing contact assemblies (340, 350) respectively, are magnetically attracted to each other. It should be understood that the magnetic attraction between bodies (336, 338) while cartridge (304) is coupled with channel (302) is strong enough to maintain the elastic deformation of elastomeric cover (344) such that contacts (342, 352) may remain electrically coupled with each other. Elastomeric (344) may also create a fluid tight seal between contacts (342, 352) while electrically coupled such that additional fluid (F) may not interfere with the electrical connection between contacts (342, 352). Once cartridge (334) is removed, the elastic nature of cover (344) will return to a fluid right seal protecting contacts (342) from exposure to additional fluid (F).

Figure 19:
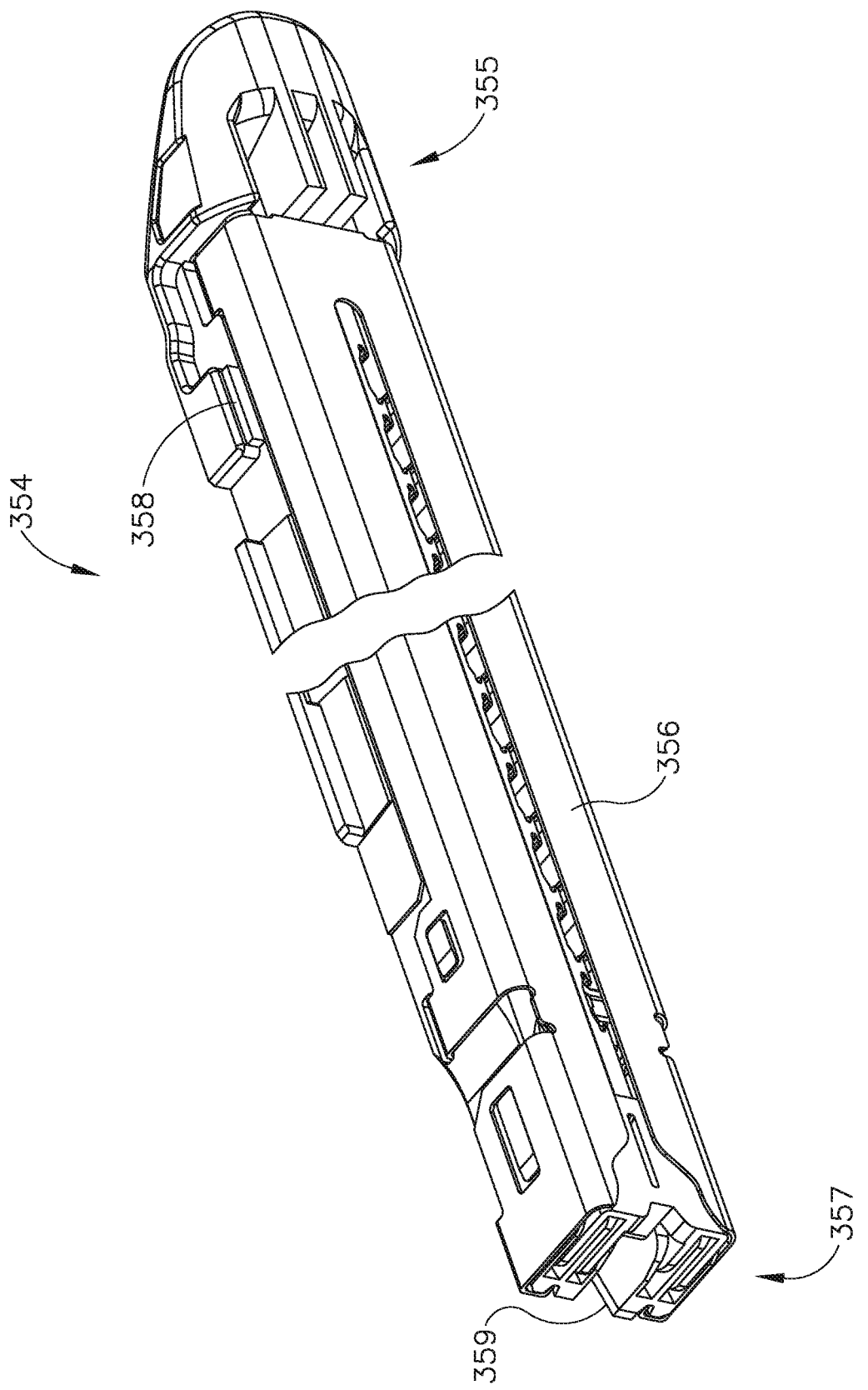
FIG. 19 depicts a perspective view of an alternative cartridge that may be readily incorporated into the end effector of FIG. 8.
Figure 20:
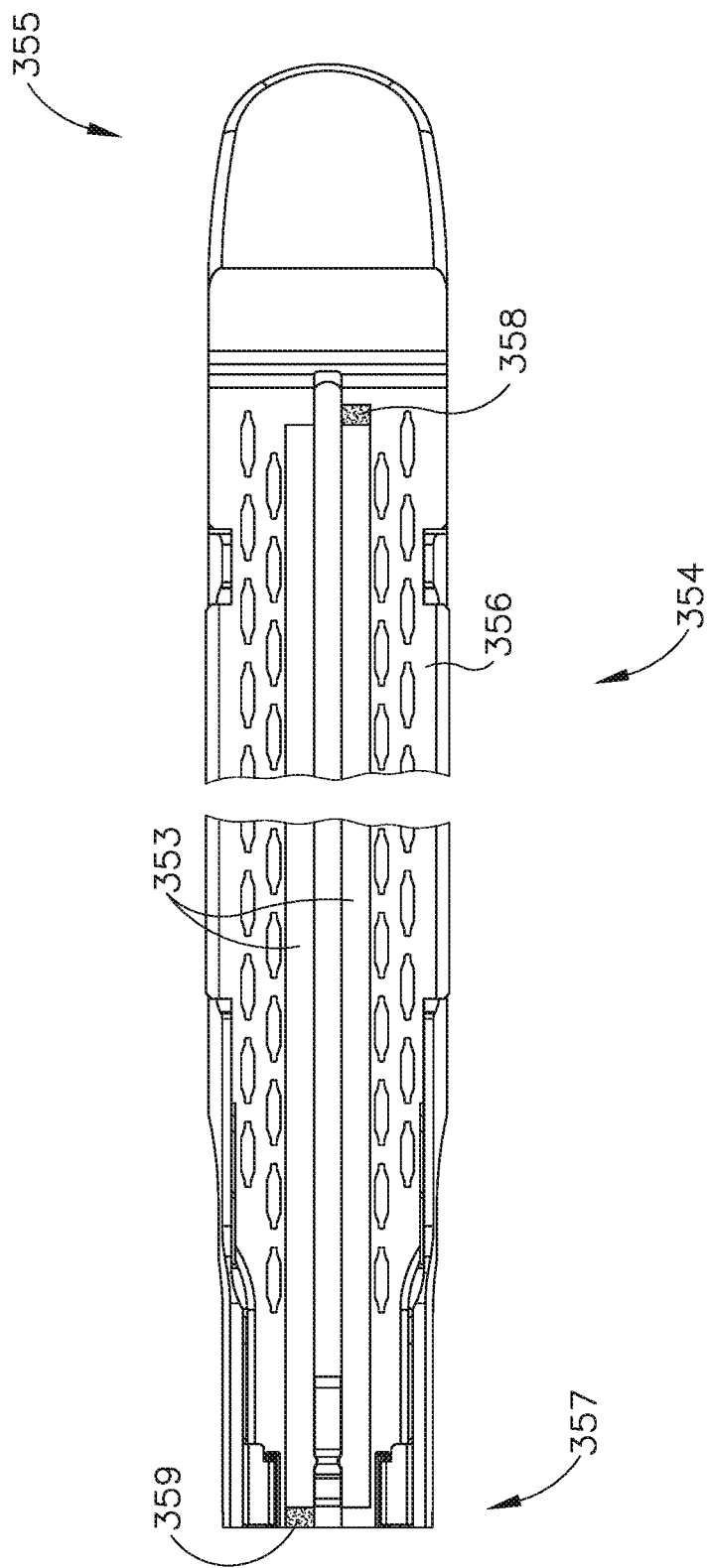
FIG. 20 depicts a top plan view of the cartridge of FIG. 19.

FIGS. 19-20 show an alternative cartridge assembly (354) that may be readily incorporated into end effector (160) described above, in replacement of cartridge (164) described above. Cartridge assembly (354) may be substantially similar to cartridge (164) described above, with differences elaborated below. Cartridge (354) includes a body (356) extending from a proximal end (357) to a distal end (355), a hot contact (358), a return contact (359), and a therapeutic region (353) extending between contacts (358, 359). Contacts (358, 359) are space away from each other such that hot contact (358) is associated with proximal end (357) while return contact (359) is associated with distal end (355). Therefore, the distance between contacts (358, 359) may help prevent fluid from bringing the connection between contacts (358, 359), which may in turn prevent a short circuit. If a short circuit does occur, however, it may occur through the therapeutic regions (356).

Figure 21:
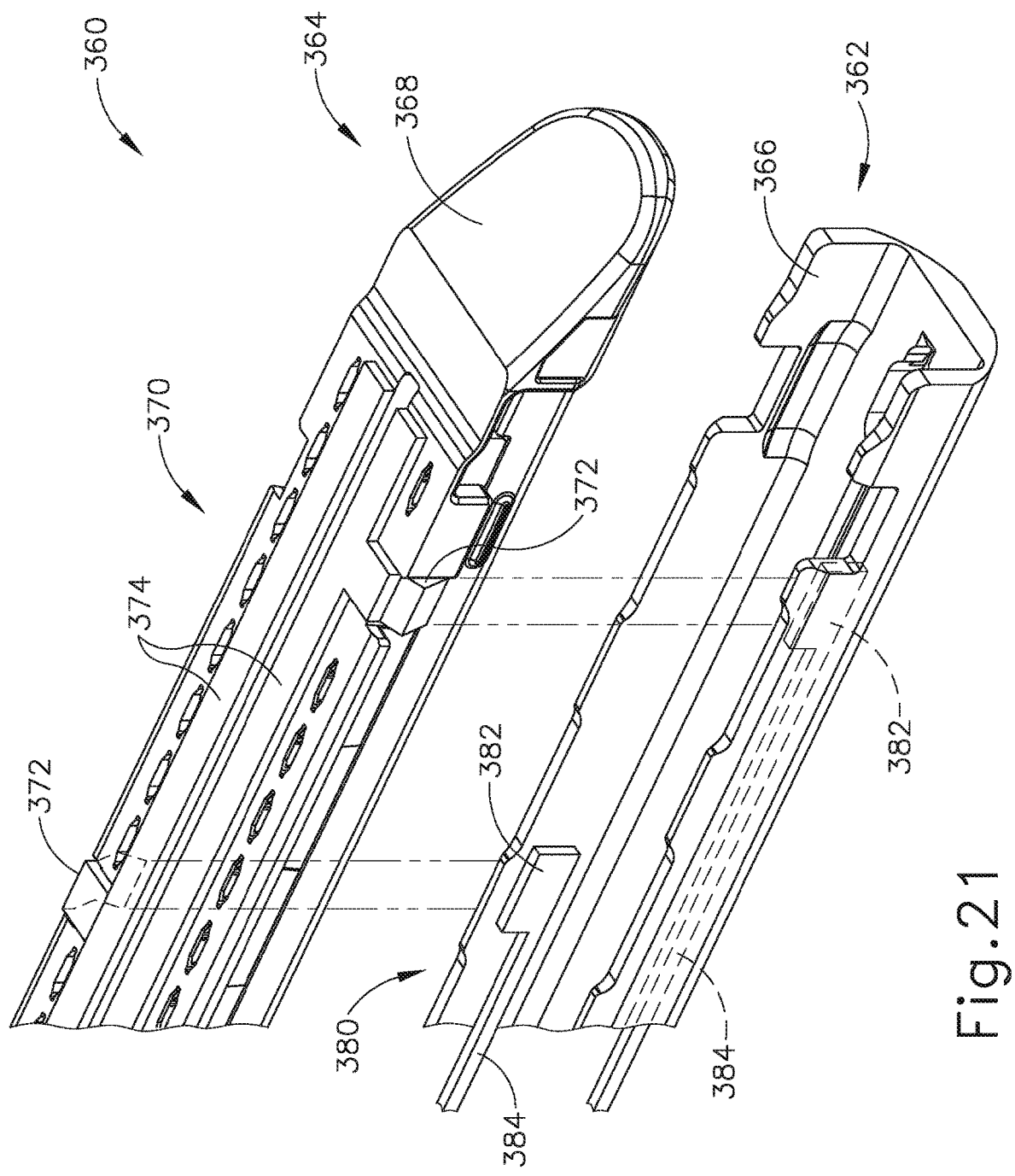
FIG. 21 depicts an exploded perspective view of an alternative cartridge and channel assembly that may be readily incorporated into the end effector of FIG. 8.

FIGS. 21-22B show an alternative exemplary cartridge and channel assembly (360) that may be readily incorporated into end effector (160) in replacement of cartridge (164) and channel (162), as described above, respectively. Cartridge and channel assembly (360) include an elongate channel (362) and a staple cartridge (364). Channel (362) and cartridge (364) are substantially similar to channel (162) and cartridge (164) as described above, respectively, with differences elaborated below. FIG. 22A shows cartridge (364) decoupled from channel (362); while FIG. 22B shows cartridge (364) fully coupled with channel (362).

Channel (362) includes a channel body (366) and a channel contact assembly (380). Channel contact assembly (380) includes any suitable number of contacts (382) as would be apparent to one having ordinary skill in the art in view of the teachings herein. In the current example, channel contact assembly (320) includes two enlarged contact pads (382) associated with opposite side walls of channel body (366). Channel contact assembly (380) also includes an electrical trace/lead (384) extending from electrical contacts (382) to shaft circuit board (134). Because electrical trace/ lead (384) extends from electrical contact (382) to shaft circuit board (134), power pack (44) may power electrical contact (382) when shaft assembly (14) is suitably coupled with handle assembly (12).

Cartridge (364) includes a cartridge body (368) and a cartridge contact assembly (370). Cartridge contact assembly (370) includes a pair of electrical contacts (372) in electrical communication with an electrically activated component (374) such that one electrical contact (372) is a hot contact and the other electrical contact (372) is a return contact. Electrical contacts (372) are configured to electrically couple with contacts (382) of channel (362) such that power pack (44) may power electrically activated component (374) when shaft assembly (14) is suitably coupled with handle assembly (12).

In the present example, enlarged contact pads (382) are located on opposite side walls of channel body (366). Additionally, enlarged contact pads (382) are located on opposite longitudinal portions of channel body (366), one being proximal and one being distal. Therefore, the increased distance based on the position of enlarged contact pads (382) may help prevent a short circuit from occurring due to fluid bridging the gap between enlarged contact pads (382). Additionally, electrical contacts (372) include a leaf spring configuration, such that electrical contacts (372) depress when coupled with enlarged contact pads (382), thereby helping ensure the electrical connection between contacts (372, 382).

FIG. 23 shows an alternative cartridge and channel assembly (400) that may be readily incorporated into end effector (160) in replacement of cartridge (164) and channel (162), as described above, respectively. Cartridge and channel assembly (400) includes an elongate channel (402) and a staple cartridge (404). Channel (402) and cartridge (404) are substantially similar to channel (462) and cartridge (464) as described above, respectively, with differences elaborated below.

Channel (402) includes a channel body (406) defining a plurality of recesses (407) and a channel contact assembly (420). Channel contact assembly (420) includes any suitable number of contacts (422) as would be apparent to one having ordinary skill in the art in view of the teachings herein. Channel contact assembly (420) also includes an electrical trace/lead (424) extending from electrical contacts (422) to shaft circuit board (134). Because electrical trace/lead (424) extends from electrical contact (422) to shaft circuit board (134), power pack (44) may power electrical contact (422) when shaft assembly (14) is suitably coupled with handle assembly (12).

Cartridge (404) includes a cartridge body (408) and a cartridge contact assembly (410). Cartridge body (408) includes a plurality of laterally extending lugs (409). Lugs (409) are dimensioned to rest within corresponding recesses (407) of channel (402) when cartridge (404) is suitably coupled with channel (402). Cartridge contact assembly (410) includes a plurality electrical contacts (412) in electrical communication with an electrically activated component (141) via connectors (416). Contacts (412) are in pairs and in communication with electrically activated component (414) such that one electrical contact (412) is a hot contact and the other electrical contact (412) is a return contact. Electrical contacts (412) are configured to electrically couple with contacts (422) of channel (402) such that power pack (44) may power electrically activated component (414) when shaft assembly (14) is suitably coupled with handle assembly (12).

Contacts (422) may be spaced away from each other such that corresponding hot and return contacts (422) are a sufficient distance along the longitudinal profile channel (402) such that it is difficult for a continuous portion of fluid to bridge a corresponding hot contact (422) and return contact (422) to create a short circuit. In other words, corresponding contacts (422) are sufficiently spaced from each other in order to reduce the likelihood fluid will create a short circuit across contacts (422). Since contacts (412) on cartridge (404) are dimensioned to correspond with contacts (422) on channel (402). it may also be difficult for fluid to span across corresponding contacts (412) to form a short circuit as well.

Figure 24:
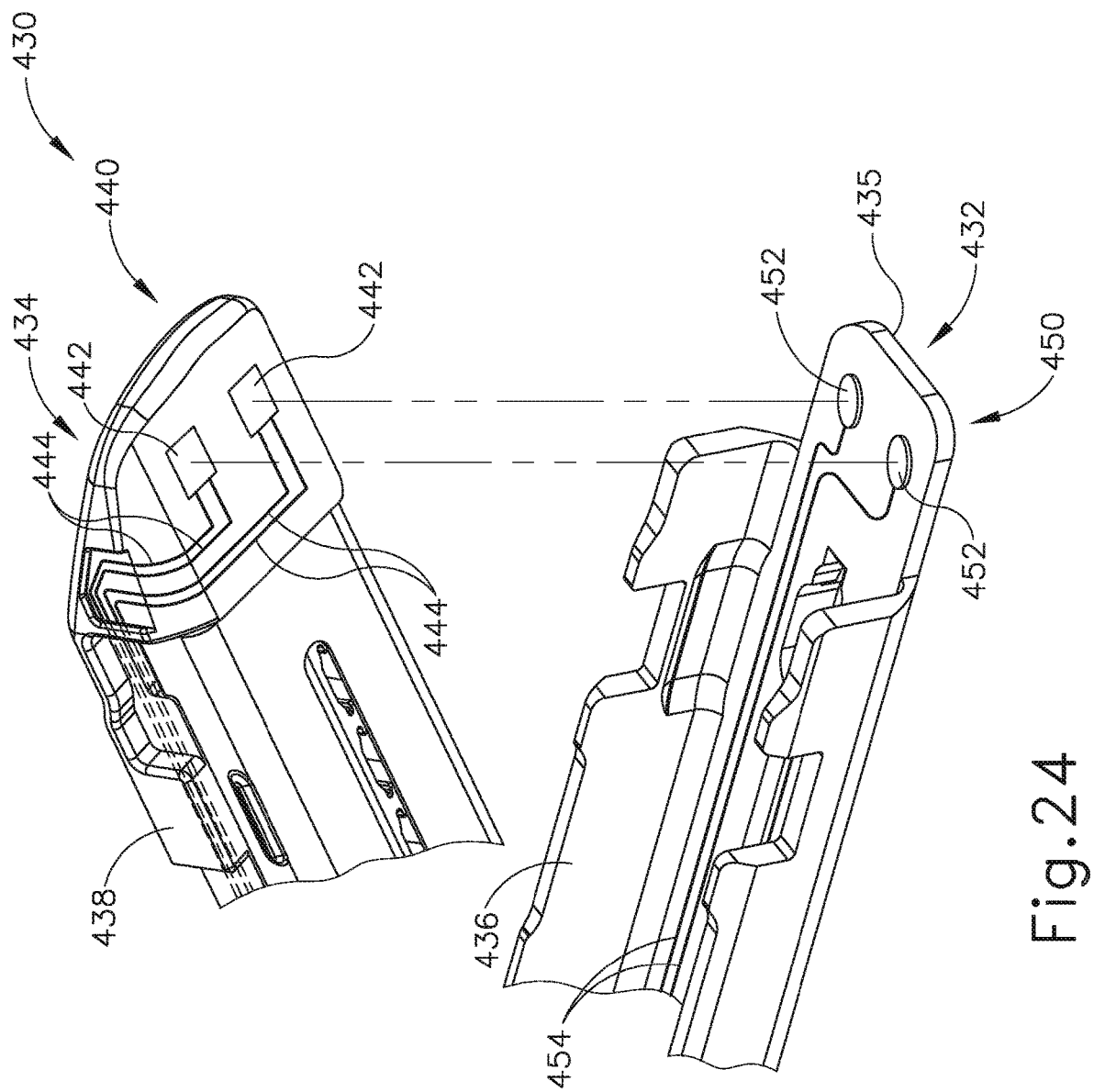
FIG. 24 depicts an exploded perspective view of an alternative cartridge and channel assembly that may be readily incorporated into the end effector of FIG. 8.

FIG. 24 show an alternative cartridge and channel assembly (430) that may be readily incorporated into end effector (160) in replacement of cartridge (164) and channel (162), as described above, respectively. Cartridge and channel assembly (430) include an elongate channel (432) and a staple cartridge (434). Channel (432) and cartridge (434) are substantially similar to channel (162) and cartridge (164) as described above, respectively, with differences elaborated below.

Channel (432) includes a channel body (436) having a distally extending tongue (435) extending from the base portion of channel body (436), and a channel contact assembly (450). Channel contact assembly (450) includes any suitable number of contacts (452) as would be apparent to one having ordinary skill in the art in view of the teachings herein. Channel contact assembly (450) also includes an electrical trace/lead (454) extending from electrical contacts (452) to shaft circuit board (134). Because electrical trace/lead (454) extends from electrical contact (452) to shaft circuit board (134), power pack (44) may power electrical contact (452) when shaft assembly (14) is suitably coupled with handle assembly (12).

Cartridge (434) includes a cartridge body (438) and a cartridge contact assembly (440). Cartridge contact assembly (440) includes a plurality electrical contacts (442) in electrical communication with an electrically activated component (not shown) via connectors (444). Contacts (442) are in pairs and in communication with electrically activated component (not show) such that one electrical contact (442) is a hot contact and the other electrical contact (442) is a return contact. Electrical contacts (442) are configured to electrically couple with contacts (452) of channel (432) such that power pack (44) may power electrically activated component (not shown) when shaft assembly (14) is suitably coupled with handle assembly (12). In the current example, contacts (452) are located on distally presented tongue (435). Therefore, contacts (442) on cartridge (434) are located on body (438) such that contacts (442, 452) electrically couple at a distal end of cartridge and channel assembly (430).

Figure 25:
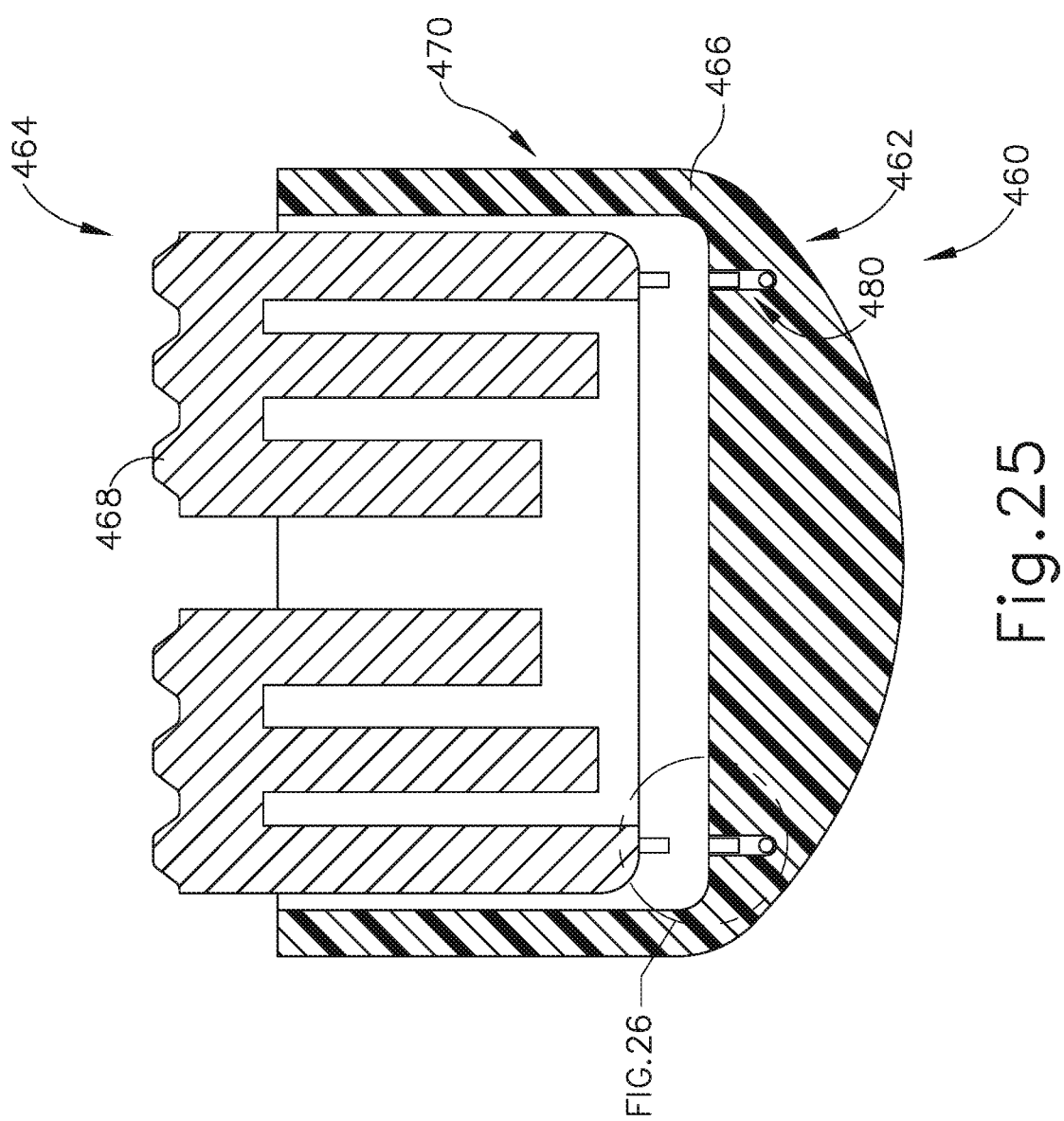
FIG. 25 depicts a cross-sectional end view of an alternative cartridge and channel assembly that may be readily incorporated into the end effector of FIG. 8, where the cartridge is decoupled from the channel.
Figure 26:
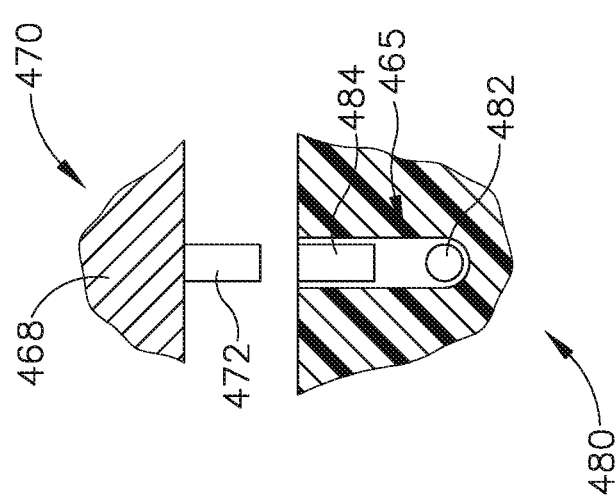
FIG. 26 depicts an enlarged cross-sectional end view of a portion of the cartridge and channel assembly of FIG. 25, where the cartridge is decoupled form the channel.

FIGS. 25-26 show an alternative exemplary cartridge and channel assembly (460) that may be readily incorporated into end effector (160) in replacement of cartridge (164) and channel (162), as described above, respectively. Cartridge and channel assembly (460) include an elongate channel (462) and a staple cartridge (464). Channel (462) and cartridge (464) are substantially similar to channel (162) and cartridge (164) as described above, respectively, with differences elaborated below.

Cartridge (464) includes a cartridge body (468) and a cartridge contact assembly (470). Cartridge contact assembly (470) includes a pair of electrical contacts (472). While not shown, electrical contacts (472) are in electrical communication with an electrically activated component (not shown) such that one electrical contact (472) is a hot contact and the other electrical contact (472) is a return contact. Electrical contacts (472) are configured to electrically couple with contacts (482) of channel (462) such that power pack (44) may power electrically activated component (not shown) when shaft assembly (14) is suitably coupled with handle assembly (12).

Channel (462) includes a channel body (466) having a base portion defining a recess (465), and a channel contact assembly (480). Channel contact assembly (480) includes an electrical contact (482) housed within the bottom of recess (465) and a floating conductive feature (484) slidably disposed within recess (465). While not specifically shown, channel contact assembly (480) includes an electrical trace/lead (not shown) extending from electrical contact (482) to shaft circuit board (134). Because electrical trace/lead (not shown) extends from electrical contact (482) to shaft circuit board (134), power pack (44) may power electrical contact (482) when shaft assembly (14) is suitably coupled with handle assembly (12). Floating conductive feature (484) floats within recess (465) and naturally floats to the top of recess (465). Floating conductive feature (484) may slide within recess (465) in order to make contact with electrical contact (482). In particular, floating conductive feature (484) may be driven into contact with electrical contact (482) by electrical contact (472) of cartridge (464) when cartridge (464) is suitably coupled with channel (462). Floating conductive feature (484) may protect contacts (484) from exposure to fluid.

Figure 27:
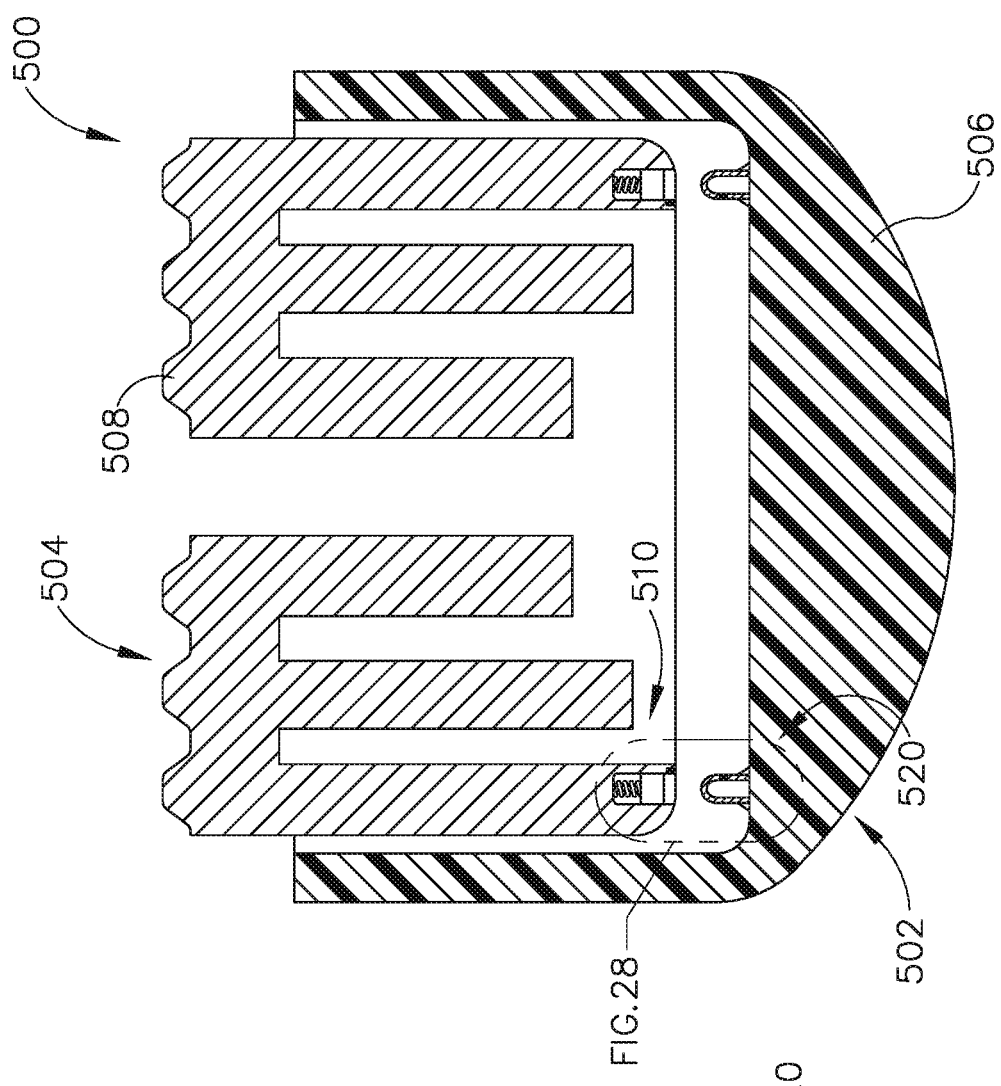
FIG. 27 depicts a cross-sectional end view of an alternative cartridge and channel assembly that may be readily incorporated into the end effector of FIG. 8, where the cartridge is decoupled from the channel.
Figure 28:
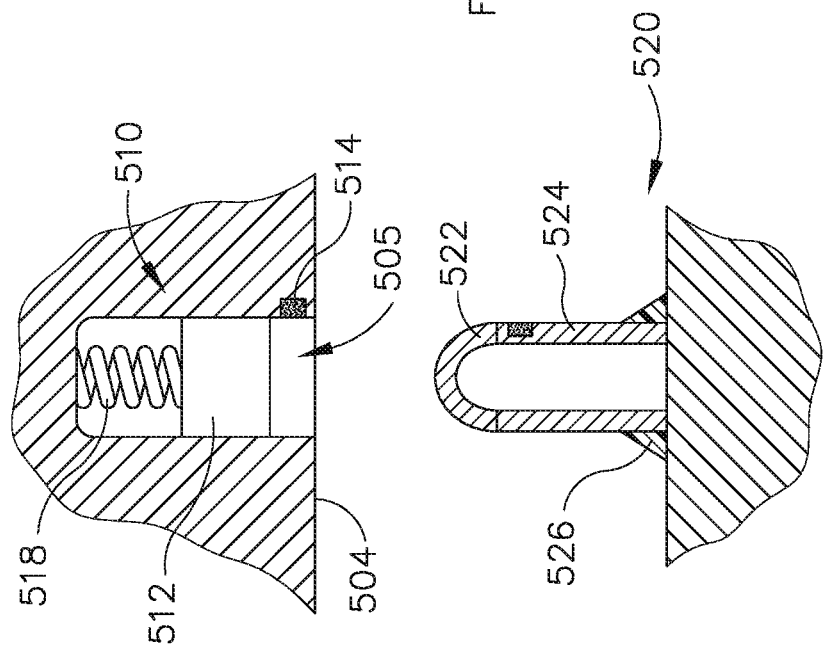
FIG. 28 depicts an enlarged cross-sectional end view of a portion of the cartridge and channel assembly of FIG. 27, where the cartridge is decoupled form the channel.

FIGS. 27-28 show an alternative exemplary cartridge and channel assembly (500) that may be readily incorporated into end effector (160) in replacement of cartridge (164) and channel (162), as described above, respectively. Cartridge and channel assembly (500) include an elongate channel (502) and a staple cartridge (504). Channel (502) and cartridge (504) are substantially similar to channel (162) and cartridge (164) as described above, respectively, with differences elaborated below.

Channel (502) includes a channel body (506) and a channel contact assembly (520). Channel contact assembly (520) includes a first contact (522), a second contact (524), and a sealing element (526). First contact (522) and second contact (524) are electrically isolated from each other and form a "headphone jack" shape such that second contact (524) extends from channel body (506) and first contact (522) terminates at the opposite end of second contact (524). first contact (522) and second contact (524) While not specifically shown, channel contact assembly (480) includes an electrical trace/lead (not shown) extending from first contact (522) and second contact (524) to shaft circuit board (134). Because electrical trace/lead (not shown) extends from first contact (522) and second contact (524) to shaft circuit board (134), power pack (44) may power first contact (522) and second contact (524) when shaft assembly (14) is suitably coupled with handle assembly (12).

Cartridge (504) includes a cartridge body (508) defining a recess (505), and a cartridge contact assembly (510). Cartridge contact assembly (510) includes a first electrical contact member (512), a second electrical contact member (514), a wiping surface (516), and a biasing spring (518). While not shown, electrical contacts (510, 512) are in electrical communication with an electrically activated component (not shown) such that one electrical contacts (510, 512) is a hot contact and the other electrical contact (510, 512) is a return contact.

First electrical contact member (512) is biased in the downward direction by biasing spring (518). Additionally, first electrical contact member (512) is slidably housed within recess (505). First electrical contact member (512) is configured to make electrical contact with first electrical contact member (522) of channel contact assembly (520) when cartridge (504) is suitably coupled with channel (502). Second electrical contact member (514) partially defines recess (505). Second electrical contact member (514) is configured to electrically couple with second electrical contacts member (524) of channel contact assembly (520) when cartridge (504) is suitably coupled with channel (502). Seal (526) is configured to prevent fluid from entering into recess (505) when cartridge (504) is suitably coupled with channel (502). Additionally, wiping surface (516) is configured to remove excess fluid from channel contact assembly (520) while cartridge (504) is being inserted into channel (502).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body comprising a power source; (b) a shaft assembly extending distally from the body; (c) an end effector at a distal end of the shaft assembly, wherein the end effector comprises: (i) a channel assembly, and (ii) a cartridge assembly configured to selectively couple with the channel assembly, wherein the cartridge assembly comprises an electrically activated component; and (d) an electrical contact assembly configured to electrically couple the power source with the electrically activated component of the cartridge assembly, wherein the electrical contact assembly comprises: (i) a first electrical contact associated with the channel assembly, (ii) a second electrical contact associated with the channel assembly, and (iii) a hydrophobic layer extending between the first electrical contact and the second electrical contact.

Example 2

The surgical instrument of Example 1, where the hydrophobic layer completely encompasses the first electrical contact.

Example 3

The surgical instrument of any one or more of Examples 1 through 2, wherein the hydrophobic layer is arranged in a matrix.

Example 4

The surgical instrument of Example 3, wherein the matrix defines a plurality of zones.

Example 5

The surgical instrument of Example 4, wherein the first electrical contact is located within a first zone in the plurality of zones, wherein the second electrical contact is located within a second zone in the plurality of zones.

Example 6

The surgical instrument of any one or more of Examples 4 through 5, wherein the first electrical contact is the only electrical contact within the first zone.

Example 7

The surgical instrument of Example 6, wherein the second electrical contact is the only electrical contact within the second zone.

Example 8

The surgical instrument of any one or more of Examples 1 through 7, wherein the channel comprises a proximal portion and a distal portion, wherein the first electrical contact is located in the proximal portion and the second electrical contact is located in the distal portion.

Example 9

The surgical instrument of any one or more of Examples 1 through 8, wherein the channel defines a first lateral recess and a second lateral recess, wherein the first electrical contact is located within the first lateral recess, wherein the second electrical contact is located within the second lateral recess.

Example 10

The surgical instrument of Example 9, wherein the channel further defines a central recess, wherein the first lateral recess is located on a first side of the central recess, wherein the second lateral recess is located on a second side of the central recess.

Example 11

The surgical instrument of any one or more of Examples 1 through 10, wherein the channel comprises a base wall and two side walls, wherein the first electrical contact and the second electrical contact are fixed to the base wall.

Example 12

The surgical instrument of any one or more of Examples 1 through 11, wherein the cartridge assembly further comprises a third electrical contact and a fourth electrical contact.

Example 13

The surgical instrument of Example 12, wherein the third electrical contact is configured to electrical couple with the first electrical contact when the cartridge assembly is coupled with the channel assembly.

Example 14

The surgical instrument of Example 13, wherein the fourth electrical contact is configured to electrically couple with the second electrical contact when the cartridge assembly is coupled with the channel assembly.

Example 15

A surgical instrument comprising: (a) a body comprising a power source; (b) a shaft assembly extending distally from the body; (c) an end effector at a distal end of the shaft assembly, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple the power source with the electrically activated component of the cartridge assembly, wherein the electrical contact assembly comprises: (i) a first electrical contact assembly, wherein the first electrical contact assembly comprises a first plurality of electrical contacts and a wiper, and (ii) a second electrical contact assembly, wherein the second electrical contact assembly comprises a second plurality of electrical contacts, wherein the wiper is configured to clean fluid from the second plurality of electrical contacts as the cartridge assembly couples with the channel assembly.

Example 16

The surgical instrument of Example 15, wherein the wiper is configured to form a seal when the cartridge assembly is coupled with the channel assembly.

Example 17

The surgical instrument of Example 16, wherein the seal is configured to prevent fluid from contacting the first plurality of electrical contacts and the second plurality of electrical contacts.

Example 18

The surgical instrument of any one or more of Examples 15 through 17, wherein the cartridge assembly comprises an absorbent section configured to collected fluid from the first plurality of electrical contacts and the second plurality of electrical contacts.

Example 19

The surgical instrument of any one or more of Examples 15 through 18, wherein the wiper has a convex surface configured to direct fluid away from the first plurality of electrical contacts and the second plurality of electrical contacts while the cartridge assembly is being coupled with the channel assembly.

Example 20

A surgical instrument comprising: (a) a body comprising a power source; (b) a shaft assembly extending distally from the body; (c) an end effector at a distal end of the shaft assembly, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple the power source with the electrically activated component of the cartridge assembly, wherein the electrical contact assembly comprises: (i) a first electrical contact assembly, wherein the first electrical contact assembly comprises a first electrical contact and a gasket, wherein the gasket is configured to prevent the first electrical contact from exposure to fluid, and (ii) a second electrical contact assembly, wherein the second electrical contact assembly comprises a second electrical contact configured to open the gasket and electrically couple with the first electrical contact when the cartridge assembly is coupled with the channel assembly.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. App. No. 15/934,139, entitled "Surgical Instrument with Compressible Electrical Connector," filed on Mar. 23, 2018, published as U.S. Pub. No. 2019/0290307 on Sep. 26, 2019; U.S. App. No. 15/934,148 , entitled "Seal for Surgical Instrument," filed on Mar. 23, 2018, published as U.S. Pub. No. 2019/0290308 on Sep. 26, 2019; U.S. App. No. 15/934,160 entitled "Surgical Instrument with Recessed Contacts and Electrically Insulting Barriers," filed on Mar. 23, 2018, published as U.S. Pub. No. 2019/0290269 on Sep. 26, 2019; U.S. App. No. 15/934,166, entitled "Surgical Instrument with Electrical Contact Under Membrane," filed on Mar. 23, 2018, published as U.S. No. 2019/0290270 on Sep. 26, 2019; U.S. App. No. 15/934,180, entitled "Surgical Instrument with Capacitive Electrical Interface," filed on Mar. 23, 2018, published as U.S. Pub. No. 2019/0290272 on Sep. 26, 2019; and U.S. App. No. 15/934,190, entitled "Slip Ring Assembly for Surgical Instrument," filed on Mar. 23, 2018, published as U.S. Pub. No. 2019/0290273 on Sep. 26, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body comprising a power source;
   (b) a shaft assembly extending distally from the body;
   (c) an end effector at a distal end of the shaft assembly, wherein the end effector comprises:
      (i) a channel assembly, and
      (ii) a cartridge assembly configured to selectively couple with the channel assembly, wherein the cartridge assembly comprises an electrically activated component; and
   (d) an electrical contact assembly configured to electrically couple the power source with the electrically activated component of the cartridge assembly, wherein the electrical contact assembly comprises:
      (i) a first electrical contact associated with the channel assembly,
      (ii) a second electrical contact associated with the channel assembly, and
      (iii) a hydrophobic layer extending between the first electrical contact and the second electrical contact.

2. The surgical instrument of claim 1, where the hydrophobic layer completely encompasses the first electrical contact.

3. The surgical instrument of claim 1, wherein the hydrophobic layer is arranged in a matrix.

4. The surgical instrument of claim 3, wherein the matrix defines a plurality of zones.

5. The surgical instrument of claim 4, wherein the first electrical contact is located within a first zone in the plurality of zones, wherein the second electrical contact is located within a second zone in the plurality of zones.

6. The surgical instrument of claim 4, wherein the first electrical contact is the only electrical contact within the first zone.

7. The surgical instrument of claim 6, wherein the second electrical contact is the only electrical contact within the second zone.

8. The surgical instrument of claim 1, wherein the channel comprises a proximal portion and a distal portion, wherein the first electrical contact is located in the proximal portion and the second electrical contact is located in the distal portion.

9. The surgical instrument of claim 1, wherein the channel defines a first lateral recess and a second lateral recess, wherein the first electrical contact is located within the first lateral recess, wherein the second electrical contact is located within the second lateral recess.

10. The surgical instrument of claim 9, wherein the channel further defines a central recess, wherein the first lateral recess is located on a first side of the central recess, wherein the second lateral recess is located on a second side of the central recess.

11. The surgical instrument of claim 1, wherein the channel comprises a base wall and two side walls, wherein the first electrical contact and the second electrical contact are fixed to the base wall.

12. The surgical instrument of claim 1, wherein the cartridge assembly further comprises a third electrical contact and a fourth electrical contact.

13. The surgical instrument of claim 12, wherein the third electrical contact is configured to electrical couple with the first electrical contact when the cartridge assembly is coupled with the channel assembly.

14. The surgical instrument of claim 13, wherein the fourth electrical contact is configured to electrically couple with the second electrical contact when the cartridge assembly is coupled with the channel assembly.

15. A surgical instrument comprising:
   (a) a body comprising a power source;
   (b) a shaft assembly extending distally from the body;
   (c) an end effector at a distal end of the shaft assembly, wherein the end effector comprises:
      (i) a channel assembly, and
      (ii) a cartridge assembly configured to selectively couple with the channel assembly, wherein the cartridge assembly comprises an electrically activated component; and
   (d) an electrical contact assembly configured electrically couple the power source with the electrically activated component of the cartridge assembly, wherein the electrical contact assembly comprises:
(i) a first electrical contact assembly, wherein the first electrical contact assembly comprises a first plurality of electrical contacts and a wiper, and
(ii) a second electrical contact assembly, wherein the second electrical contact assembly comprises a second plurality of electrical contacts, wherein the wiper is configured to clean fluid from the second plurality of electrical contacts as the cartridge assembly couples with the channel assembly.

16. The surgical instrument of claim 15, wherein the wiper is configured to form a seal when the cartridge assembly is coupled with the channel assembly.

17. The surgical instrument of claim 16, wherein the seal is configured to prevent fluid from contacting the first plurality of electrical contacts and the second plurality of electrical contacts.

18. The surgical instrument of claim 15, wherein the cartridge assembly comprises an absorbent section configured to collected fluid from the first plurality of electrical contacts and the second plurality of electrical contacts.

19. The surgical instrument of claim 15, wherein the wiper has a convex surface configured to direct fluid away from the first plurality of electrical contacts and the second plurality of electrical contacts while the cartridge assembly is being coupled with the channel assembly.

20. A surgical instrument comprising:
(a) a body comprising a power source;
(b) a shaft assembly extending distally from the body;
(c) an end effector at a distal end of the shaft assembly, wherein the end effector comprises:
(i) a channel assembly, and
(ii) a cartridge assembly configured to selectively couple with the channel assembly, wherein the cartridge assembly comprises an electrically activated component; and
(d) an electrical contact assembly configured electrically couple the power source with the electrically activated component of the cartridge assembly, wherein the electrical contact assembly comprises:
(i) a first electrical contact assembly, wherein the first electrical contact assembly comprises a first electrical contact and a gasket, wherein the gasket is configured to prevent the first electrical contact from exposure to fluid, and
(ii) a second electrical contact assembly, wherein the second electrical contact assembly comprises a second electrical contact configured to open the gasket and electrically couple with the first electrical contact when the cartridge assembly is coupled with the channel assembly.

\* \* \* \* \*